(12) United States Patent
Levy

(10) Patent No.: US 12,004,793 B2
(45) Date of Patent: Jun. 11, 2024

(54) BI-SPRING SURGICAL HAMMER IMPACT TOOLS

(71) Applicant: Zimmer, Inc., Warsaw, IN (US)

(72) Inventor: David Levy, Berkeley, CA (US)

(73) Assignee: Zimmer, Inc., Warsaw, IN (US)

( * ) Notice: Subject to any disclaimer, the term of this patent is extended or adjusted under 35 U.S.C. 154(b) by 236 days.

(21) Appl. No.: 17/678,807

(22) Filed: Feb. 23, 2022

(65) Prior Publication Data

US 2022/0273317 A1 Sep. 1, 2022

Related U.S. Application Data

(60) Provisional application No. 63/154,219, filed on Feb. 26, 2021.

(51) Int. Cl.
*A61B 17/92* (2006.01)
*A61B 17/16* (2006.01)
*A61B 17/00* (2006.01)

(52) U.S. Cl.
CPC .......... *A61B 17/92* (2013.01); *A61B 17/1626* (2013.01); *A61B 17/1628* (2013.01);
(Continued)

(58) Field of Classification Search
CPC . A61B 17/92; A61B 17/921; A61B 2017/922; A61B 2017/924;
(Continued)

(56) References Cited

U.S. PATENT DOCUMENTS

| 974,267 A | 11/1910 | Hennessy et al. |
| 2,542,695 A | 2/1951 | Neff et al. |

(Continued)

FOREIGN PATENT DOCUMENTS

| AU | 2019203142 | 11/2019 |
| AU | 2020200771 | 2/2020 |

(Continued)

OTHER PUBLICATIONS

"International Application Serial No. PCT US2022 017537, International Search Report mailed Jun. 1, 2022", 4 pages.

(Continued)

*Primary Examiner* — Eric S Gibson
(74) *Attorney, Agent, or Firm* — SCHWEGMAN LUNDBERG & WOESSNER, P.A.

(57) ABSTRACT

Disclosed herein are bi-spring surgical hammer impact tools and methods of use thereof. The bi-spring surgical hammer impact tools can include an elongated drive rod disposed in the housing and including an impact flange in a mid-region thereof. A tool implement can be mounted to a first end of the elongated drive rod. An impact shuttle can be mounted on the elongated drive rod and can include first and second impact surfaces opposing opposite faces of the impact flange. A plurality of annular teeth can be defined by an exterior surface of the impact shuttle. First and second springs can be disposed against opposite ends of the impact shuttle. A partial tooth pinion attached to a drive shaft and movable for engagement with the plurality of annular teeth of the impact shuttle can be included.

20 Claims, 17 Drawing Sheets

(52) U.S. Cl.
CPC ............... *A61B 2017/0042* (2013.01); *A61B 2017/00734* (2013.01); *A61B 2017/925* (2013.01); *A61B 2017/928* (2013.01)

(58) Field of Classification Search
CPC ........ A61B 2017/925; A61B 2017/927; A61B 2017/928
See application file for complete search history.

(56) References Cited

U.S. PATENT DOCUMENTS

| | | | |
|---|---|---|---|
| 3,450,215 A | 6/1969 | Emery | |
| 3,472,323 A | 10/1969 | Hall | |
| 3,626,935 A | 12/1971 | Pollock et al. | |
| 3,752,161 A | 8/1973 | Bent | |
| 4,298,074 A | 11/1981 | Mattchen | |
| 4,466,429 A | 8/1984 | Loscher et al. | |
| 4,651,833 A | 3/1987 | Karpf et al. | |
| 4,834,092 A | 5/1989 | Alexson et al. | |
| 5,057,112 A | 10/1991 | Sherman et al. | |
| 5,108,400 A | 4/1992 | Appel et al. | |
| 5,152,352 A | 10/1992 | Mandanis | |
| 5,163,519 A | 11/1992 | Mead et al. | |
| 5,210,918 A | 5/1993 | Wozniak et al. | |
| 5,282,805 A | 2/1994 | Richelsoph et al. | |
| 5,352,230 A | 10/1994 | Hood | |
| 5,353,230 A | 10/1994 | Maejima et al. | |
| 5,431,660 A | 7/1995 | Burke | |
| 5,485,887 A | 1/1996 | Mandanis | |
| 5,553,675 A | 9/1996 | Pitzen et al. | |
| 6,126,694 A | 10/2000 | Gray, Jr. | |
| 6,159,214 A | 12/2000 | Michelson | |
| 6,264,660 B1 | 7/2001 | Schmidt et al. | |
| 6,264,661 B1 | 7/2001 | Jerger et al. | |
| 6,368,324 B1 | 4/2002 | Dinger | |
| 6,520,266 B2 | 2/2003 | Bongers-Ambrosius et al. | |
| 6,626,913 B1 | 9/2003 | Mckinnon et al. | |
| 6,814,738 B2 | 11/2004 | Naughton et al. | |
| 6,868,918 B2 | 3/2005 | Shinohara | |
| 7,090,677 B2 | 8/2006 | Fallin et al. | |
| 7,189,241 B2 | 3/2007 | Yoon et al. | |
| 7,637,327 B2 | 12/2009 | Grünig | |
| 8,002,776 B2 | 8/2011 | Liu et al. | |
| 8,393,409 B2 | 3/2013 | Pedicini | |
| 8,444,647 B2 | 5/2013 | Walen et al. | |
| 8,465,492 B2 | 6/2013 | Estes | |
| 8,556,901 B2 | 10/2013 | Anthony et al. | |
| 8,602,124 B2 | 12/2013 | Pedicini | |
| 8,695,726 B2 | 4/2014 | Pedicini | |
| 8,894,654 B2 | 11/2014 | Anderson | |
| 8,936,105 B2 | 1/2015 | Pedicini | |
| 8,936,106 B2 | 1/2015 | Pedicini | |
| 9,168,154 B2 | 10/2015 | Behzadi | |
| 9,186,158 B2 | 11/2015 | Anthony et al. | |
| 9,198,675 B2 | 12/2015 | Nelson et al. | |
| 9,220,612 B2 | 12/2015 | Behzadi | |
| 9,554,965 B2 | 1/2017 | Foehrenbach | |
| 9,629,641 B2 | 4/2017 | Ferro et al. | |
| 9,649,202 B2 | 5/2017 | Behzadi et al. | |
| 9,877,734 B2 | 1/2018 | Anderson | |
| 9,901,354 B2 | 2/2018 | Pedicini | |
| 9,931,151 B2 | 4/2018 | Donald et al. | |
| 9,943,318 B2 | 4/2018 | Anthony et al. | |
| RE46,954 E | 7/2018 | Pedicini | |
| 10,028,754 B2 | 7/2018 | Johnson et al. | |
| RE46,979 E | 8/2018 | Pedicini | |
| 10,159,500 B2 | 12/2018 | Chavarria et al. | |
| 10,172,722 B2 | 1/2019 | Behzadi | |
| 10,245,160 B2 | 4/2019 | Behzadi | |
| 10,245,162 B2 | 4/2019 | Behzadi | |
| 10,251,663 B2 | 4/2019 | Behzadi | |
| 10,299,930 B2 | 5/2019 | Behzadi | |
| 10,342,591 B2 | 7/2019 | Pedicini | |
| 10,368,882 B2 | 8/2019 | Ferro et al. | |
| 10,413,425 B2 | 9/2019 | Behzadi | |
| 10,426,540 B2 | 10/2019 | Behzadi | |
| 10,441,244 B2 | 10/2019 | Behzadi | |
| 10,456,271 B2 | 10/2019 | Behzadi | |
| 10,463,505 B2 | 11/2019 | Behzadi | |
| 10,470,897 B2 | 11/2019 | Behzadi | |
| 10,478,318 B2 | 11/2019 | Behzadi | |
| 10,568,643 B2 | 2/2020 | Johnson et al. | |
| 10,603,173 B2 | 3/2020 | Carr et al. | |
| RE47,963 E | 4/2020 | Pedicini | |
| 10,610,379 B2 | 4/2020 | Behzadi | |
| RE47,997 E | 5/2020 | Pedicini | |
| 10,653,533 B2 | 5/2020 | Behzadi | |
| 10,660,767 B2 | 5/2020 | Behzadi | |
| 10,729,559 B2 | 8/2020 | Behzadi et al. | |
| RE48,184 E | 9/2020 | Pedicini | |
| RE48,251 E | 10/2020 | Pedicini | |
| 11,013,503 B2 | 5/2021 | Pedicini | |
| 11,490,943 B2 | 11/2022 | Haiat et al. | |
| 11,918,268 B2 | 3/2024 | Doyle | |
| 11,925,359 B2 | 3/2024 | Slocum et al. | |
| 2010/0137760 A1 | 6/2010 | Schulz et al. | |
| 2011/0270256 A1 | 11/2011 | Nelson et al. | |
| 2012/0172939 A1 | 7/2012 | Pedicini | |
| 2012/0215267 A1 | 8/2012 | Pedicini | |
| 2012/0259339 A1 | 10/2012 | Hood et al. | |
| 2013/0161050 A1 | 6/2013 | Pedicini | |
| 2013/0261681 A1 | 10/2013 | Bittenson | |
| 2014/0318819 A1 | 10/2014 | Pedicini | |
| 2014/0318823 A1 | 10/2014 | Pedicini | |
| 2015/0196343 A1 | 7/2015 | Donald et al. | |
| 2016/0199199 A1 | 7/2016 | Pedicini | |
| 2017/0020536 A1 | 1/2017 | Johnson et al. | |
| 2018/0055518 A1* | 3/2018 | Pedicini | A61B 17/17 |
| 2018/0055552 A1* | 3/2018 | Pedicini | A61B 17/92 |
| 2018/0318089 A1 | 11/2018 | Carr et al. | |
| 2018/0360464 A1 | 12/2018 | Irvine | |
| 2019/0167434 A1 | 6/2019 | Satterthwaite et al. | |
| 2019/0183554 A1 | 6/2019 | Pedicini | |
| 2019/0247057 A1 | 8/2019 | Anderson | |
| 2019/0282286 A1 | 9/2019 | Pedicini | |
| 2022/0142693 A1* | 5/2022 | Slocum | A61F 2/46 |
| 2022/0226033 A1 | 7/2022 | Slocum et al. | |
| 2022/0240946 A1 | 8/2022 | Slocum et al. | |
| 2022/0240947 A1 | 8/2022 | Marinkovich | |
| 2022/0240998 A1* | 8/2022 | Slocum | A61B 17/1659 |
| 2022/0273317 A1* | 9/2022 | Levy | A61B 17/1628 |
| 2023/0240735 A1 | 8/2023 | Doyle | |
| 2024/0024012 A1 | 1/2024 | Dittrich et al. | |

FOREIGN PATENT DOCUMENTS

| | | | | |
|---|---|---|---|---|
| AU | 2017320580 B2 * | 4/2023 | | A61B 17/1604 |
| AU | 2021378282 A1 * | 6/2023 | | A61B 17/92 |
| AU | 2022227599 A1 * | 8/2023 | | A61B 17/1624 |
| CA | 3063569 A1 * | 11/2018 | | A61B 17/025 |
| CA | 3209081 A1 * | 8/2022 | | A61B 17/1659 |
| CA | 3211071 A1 * | 9/2022 | | A61B 17/1624 |
| CH | 701397 A2 | 1/2011 | | |
| CN | 2423872 Y | 3/2001 | | |
| CN | 204863450 U | 12/2015 | | |
| CN | 108602180 A * | 9/2018 | | A61B 17/1604 |
| CN | 109070324 A * | 12/2018 | | A61B 17/1604 |
| CN | 116801840 A | 9/2023 | | |
| CN | 117414174 | 1/2024 | | |
| DE | 102010017726 | 1/2011 | | |
| EP | 0290375 A1 | 11/1988 | | |
| FR | 2054809 A5 | 5/1971 | | |
| JP | 7127068 B2 * | 8/2022 | | A61B 17/025 |
| JP | 2022166207 A * | 11/2022 | | A61B 17/025 |
| JP | 7366968 B2 * | 10/2023 | | A61B 17/1604 |
| JP | 7375104 B2 * | 11/2023 | | A61B 17/1604 |
| JP | 7404463 B2 * | 12/2023 | | A61B 17/025 |
| JP | 2023551117 | 12/2023 | | |
| JP | 2024013234 | 1/2024 | | |
| JP | 2024504977 | 2/2024 | | |
| JP | 2024505231 | 2/2024 | | |
| JP | 2024505239 | 2/2024 | | |
| JP | 2024505543 | 2/2024 | | |
| JP | 2024507954 | 2/2024 | | |

(56) References Cited

FOREIGN PATENT DOCUMENTS

| WO | WO-8802246 | A2 |   | 4/1988 |   |
|---|---|---|---|---|---|
| WO | WO-8906516 | A1 |   | 7/1989 |   |
| WO | WO-2008130904 | A2 |   | 10/2008 |   |
| WO | WO-2016112397 | A1 |   | 7/2016 |   |
| WO | WO-2018044348 | A1 |   | 3/2018 |   |
| WO | WO-2018044348 | A1 | * | 3/2018 | ......... A61B 17/1604 |
| WO | WO-2018217250 | A1 |   | 11/2018 |   |
| WO | WO-2022103835 | A1 | * | 5/2022 | ............ A61B 17/92 |
| WO | WO-2022103835 | A1 |   | 5/2022 |   |
| WO | WO-2022159704 | A1 |   | 7/2022 |   |
| WO | WO-2022165215 | A1 |   | 8/2022 |   |
| WO | WO-2022165223 | A1 |   | 8/2022 |   |
| WO | WO-2022165357 | A1 |   | 8/2022 |   |
| WO | WO-2022165357 | A1 | * | 8/2022 | ......... A61B 17/1659 |
| WO | WO-2022182772 | A1 |   | 9/2022 |   |
| WO | WO-2022182772 | A1 | * | 9/2022 | ......... A61B 17/1624 |

OTHER PUBLICATIONS

"International Application Serial No. PCT US2022 017537, Written Opinion mailed Jun. 1, 2022", 5 pages.
U.S. Appl. No. 17/523,540, filed Nov. 10, 2021, Bi-Spring Surgical Impact Tool.
U.S. Appl. No. 17/581,316, filed Jan. 21, 2022, Linear Electric Surgical Hammer Impact Tool.
U.S. Appl. No. 17/587,794, filed Jan. 28, 2022, Rotary Electric Surgical Hammer Impact Tool.
U.S. Appl. No. 17/587,866, filed Jan. 28, 2022, Orthopedic Impactor Tool.
U.S. Appl. No. 17/589,456, filed Jan. 31, 2022, Tri-Roll Thread Electric Surgical Impact Tool.
"U.S. Appl. No. 17/587,794, Response filed Aug. 28, 2023 to Restriction Requirement mailed Jun. 27, 2023", 7 pgs.
"U.S. Appl. No. 17/587,794, Restriction Requirement mailed Jun. 27, 2023", 7 pgs.
"International Application Serial No. PCT/US2021/058776, International Preliminary Report on Patentability mailed May 25, 2023", 10 pgs.
"International Application Serial No. PCT/US2022/013312, International Preliminary Report on Patentability mailed Aug. 3, 2023", 12 pgs.
"International Application Serial No. PCT/US2022/014368, International Preliminary Report on Patentability mailed Aug. 10, 2023", 10 pgs.
"International Application Serial No. PCT/US2022/014380, International Preliminary Report on Patentability mailed Aug. 10, 2023", 9 pgs.
"International Application Serial No. PCT/US2022/014596, International Preliminary Report on Patentability mailed Aug. 10, 2023", 7 pgs.
"International Application Serial No. PCT/US2022/017537, International Preliminary Report on Patentability mailed Sep. 7, 2023", 7 pgs.
"International Application Serial No. PCT/US2021/058776, International Search Report mailed Feb. 9, 2022", 5 pgs.
"International Application Serial No. PCT/US2021/058776, Written Opinion mailed Feb. 9, 2022", 8 pgs.
"International Application Serial No. PCT/US2022/013312, International Search Report mailed Jun. 24, 2022", 6 pgs.
"International Application Serial No. PCT/US2022/013312, Invitation to Pay Additional Fees mailed May 3, 2022", 5 pgs.
"International Application Serial No. PCT/US2022/013312, Written Opinion mailed Jun. 24, 2022", 10 pgs.
"International Application Serial No. PCT/US2022/014368, International Search Report mailed May 30, 2022", 7 pgs.
"International Application Serial No. PCT/US2022/014368, Invitation to Pay Additional Fees mailed Apr. 5, 2022", 10 pgs.
"International Application Serial No. PCT/US2022/014368, Written Opinion mailed May 3, 2022", 8 pgs.
"International Application Serial No. PCT/US2022/014380, International Search Report mailed Jun. 24, 2022", 6 pgs.
"International Application Serial No. PCT/US2022/014380, Invitation to Pay Additional Fees mailed May 3, 2022", 5 pgs.
"International Application Serial No. PCT/US2022/014380, Written Opinion mailed Jun. 24, 2022", 7 pgs.
"International Application Serial No. PCT/US2022/014596, International Search Report mailed May 10, 2022", 4 pgs.
"International Application Serial No. PCT/US2022/014596, Written Opinion mailed May 10, 2022", 5 pgs.
Budimir, Miles, "What is a rack and roller pinion?", [Online]. Retrieved from the Internet: <https://www.motioncontroltips.com/rack-roller-pinion/>, (Nov. 10, 2017), 13 pgs.
Nexen, "Rack and Roller Pinion System", [Online]. Retrieved from the Internet: <https://www.nexengroup.com/nxn/products/prod-nav/lp/Roller+Pinion+System>, (Accessed online Apr. 27, 2021), 10 pgs.
U.S. Appl. No. 18/222,830, filed Jul. 17, 2023, Linear Electric Surgical Hammer Impact Tool.
"U.S. Appl. No. 17/587,794, Notice of Allowance mailed Nov. 15, 2023", 10 pgs.
"European Application Serial No. 23186404.2, Extended European Search Report mailed Nov. 23, 2023", 8 pgs.
"European Application Serial No. 21820393.3, Response Filed Dec. 14, 2023 to Communication pursuant to Rules 161(1) and 162 EPC mailed Jul. 6, 2023", 10 pgs.
"U.S. Appl. No. 17/587,866, Notice of Allowance mailed Apr. 11, 2024", 17 pgs.
"Australian Application Serial No. 2021378282, First Examination Report mailed Mar. 7, 2024", 3 pgs.

* cited by examiner

BI-SPRING SURGICAL HAMMER IMPACT TOOLS

PRIORITY CLAIM

The present application claims priority to U.S. Provisional Application No. 63/154,219, entitled "Bi-Spring Power Impact Tool with Force Control," filed on Feb. 26, 2021; the contents of which are hereby incorporated by reference in their entirety.

FIELD OF THE DISCLOSURE

The present disclosure relates generally to surgical instruments and use thereof. More specifically, the present disclosure relates to bi-spring surgical impact tools and methods of use thereof.

BACKGROUND

Orthopedic surgeons commonly utilize tools for cutting or carving bone that require a hammer or mallet to transmit an impaction force to the tool. An example is a broach tool used to prepare the proximal end of a femur to receive the stem of a hip implant. Such broaches can be used with a hammer wielded by the physician or with a pneumatic "jackhammer" like tool. However, striking a broach tool with a hammer can be tiresome and can cause high stresses on the physician's own joints, such as the shoulder joint. Furthermore, pneumatic impact tools require connection to an air hose, which can be inconvenient and can potentially limit the physician's ability to orient the tool in the desired manner.

SUMMARY

The following, non-limiting examples, detail certain aspects of the present subject matter to solve the challenges and provide the benefits discussed herein, among others.

Example 1 is a bi-spring surgical impact tool comprising: a housing; an elongated drive rod disposed in the housing and including an impact flange in a mid-region thereof; a tool implement mounted to a first end of the elongated drive rod; an impact shuttle mounted on the elongated drive rod and including first and second impact surfaces opposing opposite faces of the impact flange and including a plurality of annular teeth on an exterior surface; a first spring disposed against a first end of the impact shuttle; a second spring disposed against a second end of the impact shuttle; a motor having a drive shaft; and a partial tooth pinion attached to the drive shaft and movable for engagement with the plurality of annular teeth of the impact shuttle.

In Example 2, the subject matter of Example 1 optionally includes wherein the housing includes a handle and further comprising a battery pack mountable to the handle.

In Example 3, the subject matter of any one or more of Examples 1-2 optionally include wherein the drive rod is supported by a rear end cap and a forward end cap of the housing.

In Example 4, the subject matter of any one or more of Examples 1-3 optionally include wherein the impact shuttle is supported on the elongated drive rod by a forward bearing and a rearward bearing.

In Example 5, the subject matter of any one or more of Examples 1-4 optionally include wherein the first spring and the second spring are formed integrally with the impact shuttle.

In Example 6, the subject matter of any one or more of Examples 1-5 optionally include wherein a rear end of the elongated drive rod includes a stop collar at a rear end thereof.

In Example 7, the subject matter of any one or more of Examples 1-6 optionally include a motor block supporting a pair of bearings that support the drive shaft of the motor and defining an opening for receiving the elongated drive rod and the impact shuttle therein.

In Example 8, the subject matter of any one or more of Examples 1-7 optionally include a force control mechanism for adjusting a force level of the impact tool by selectively limiting an amount of travel of the elongated drive rod within the housing.

In Example 9, the subject matter of Example 8 optionally includes wherein the force control mechanism includes a shaft helix member fixed to a rear end of the drive rod and including a first helix surface that engages a corresponding second helix surface adjustably disposed within a rotary member.

In Example 10, the subject matter of Example 9 optionally includes wherein the rotary member includes a plurality of detents, the force control mechanism including a yoke supporting a ball member in engagement with the plurality of detents in order to secure the rotary member in a plurality of positions.

In Example 11, the subject matter of any one or more of Examples 9-10 optionally include wherein the shaft helix member includes a pair of first helix surfaces and the rotary member includes a pair of second helix surfaces that engage the pair of first helix surfaces.

In Example 12, the subject matter of any one or more of Examples 10-11 optionally include wherein a radius of the detent is larger than a radius of the helix surface.

In Example 13, the subject matter of any one or more of Examples 10-12 optionally include wherein a radius of the detent is approximately twice a radius of an average helix radius.

Example 14 is a bi-spring surgical impact tool comprising: a housing; an elongated drive rod disposed in the housing and including an impact flange in a mid-region thereof; a tool implement mounted to a first end of the elongated drive rod; an impact shuttle mounted on the elongated drive rod and including first and second impact surfaces opposing opposite faces of the impact flange and including a plurality of gear teeth; a first spring disposed against a first end of the impact shuttle; a second spring disposed against a second end of the impact shuttle; a motor including a drive shaft; a pinion attached to the drive shaft and movable for engagement with the plurality of gear teeth of the impact shuttle; and a force control mechanism for adjusting a force level of the impact tool by selectively limiting an amount of travel of the elongated drive rod within the housing.

In Example 15, the subject matter of Example 14 optionally includes wherein the drive rod is supported by a rear end cap and a forward end cap of the housing.

In Example 16, the subject matter of any one or more of Examples 14-15 optionally include wherein the impact shuttle is supported on the elongated drive rod by a forward bearing and a rearward bearing.

In Example 17, the subject matter of any one or more of Examples 14-16 optionally include wherein the first spring and the second spring are formed integrally with the impact shuttle.

In Example 18, the subject matter of any one or more of Examples 14-17 optionally include wherein a rear end of the elongated drive rod includes a stop collar at a rear end thereof.

In Example 19, the subject matter of any one or more of Examples 14-18 optionally include a motor block supporting a pair of bearings that support the drive shaft of the motor and including an opening for receiving the elongated drive rod and the impact shuttle therein.

In Example 20, the subject matter of any one or more of Examples 14-19 optionally include wherein the force control mechanism includes a shaft helix member fixed to a rear end of the drive rod and including a first helix surface that engages a corresponding second helix surface adjustably disposed within a rotary member.

In Example 21, the subject matter of Example 20 optionally includes wherein the rotary member includes a plurality of detents, the force control mechanism including a yoke supporting a ball member in engagement with the plurality of detents in order to secure the rotary member in a plurality of positions.

In Example 22, the subject matter of any one or more of Examples 20-21 optionally include wherein the shaft helix member includes a pair of first helix surfaces and the rotary member includes a pair of second helix surfaces that engage the pair of first helix surfaces.

In Example 23, the subject matter of any one or more of Examples 21-22 optionally include wherein a radius of the detent is larger than a radius of the helix surface.

In Example 24, the subject matter of Example 23 optionally includes wherein a radius of the detent is approximately twice a radius of an average helix radius.

In Example 25, the surgical impact tools, systems, and/or methods of any one or any combination of Examples 1-24 can optionally be configured such that all elements or options recited are available to use or select from.

BRIEF DESCRIPTION OF THE FIGURES

In the drawings, which are not necessarily drawn to scale, like numerals can describe similar components in different views. Like numerals having different letter suffixes can represent different instances of similar components. The drawings illustrate generally, by way of example, but not by way of limitation, various embodiments discussed in the present document.

Corresponding reference characters indicate corresponding parts throughout the several views. The exemplifications set out herein illustrate exemplary embodiments of the disclosure, and such exemplifications are not to be construed as limiting the scope of the disclosure in any manner.

DETAILED DESCRIPTION

As an alternative to a pneumatic piston driven system, disclosed herein are spring driven systems. Specifically, the surgical impact tools disclosed herein can include a bi-spring design. The surgical impact tools disclosed herein can include a housing that defines a cavity having a first end and a second end. A shuttle located within the cavity can define a plurality of indentations. As disclosed herein, a pinion located proximate the shuttle can have a plurality of protrusions sized to mesh with the plurality of indentations during rotation of the pinion. First and second springs can mechanically couple the housing to the shuttle. Rotation of the pinion in a first direction can translate the shuttle in a first direction towards the first end of the housing and rotation of the pinion in a second direction can translate the shuttle in a second direction towards the second end of the housing.

During use, when the protrusions and the indentations are no longer in a meshing engagement, the springs can cause the shuttle to move about a drive rod. The drive rod can be oriented along an axis of the housing and can extend from the first end of the housing to the second end of the housing. A drive rod collar can be affixed to the drive rod. An insert can be coupled to the first spring and arranged to impact the drive rod collar upon disengagement of the plurality of protrusions from the plurality of the indentations. The impact of the shuttle hitting the drive rod collar can cause the drive rod to transfer an impact force to a tool, such as a rasp, broach, etc., attached to a chuck of the surgical impact tool.

The above discussion is intended to provide an overview of subject matter of the present patent application. It is not intended to provide an exclusive or exhaustive explanation of the invention. The description below is included to provide further information about the present patent application.

Figure 1:
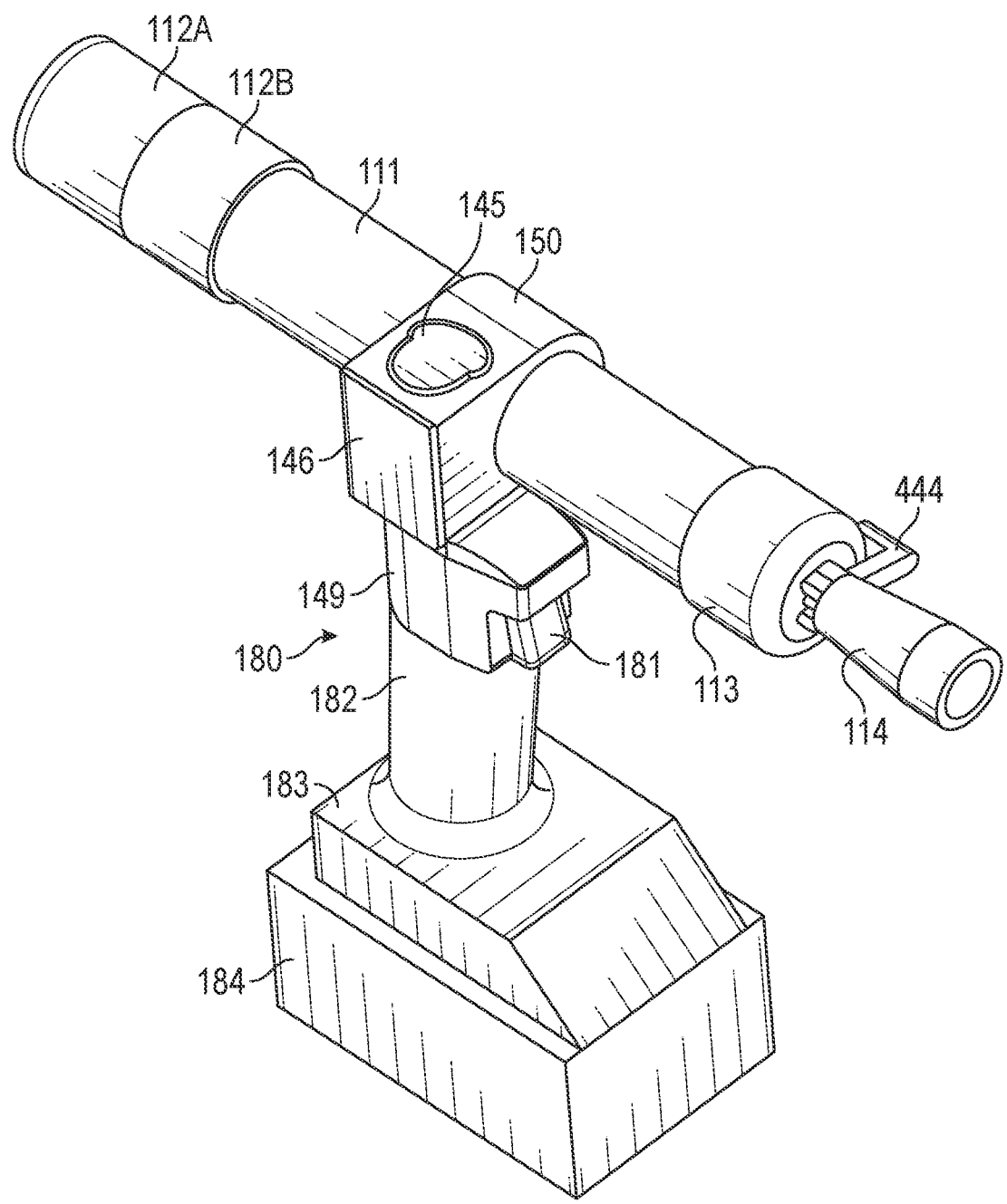
FIG. 1 shows an isometric view of an embodiment of bi-spring surgical hammer impact tool consistent with at least one example of this disclosure.
Figure 2:
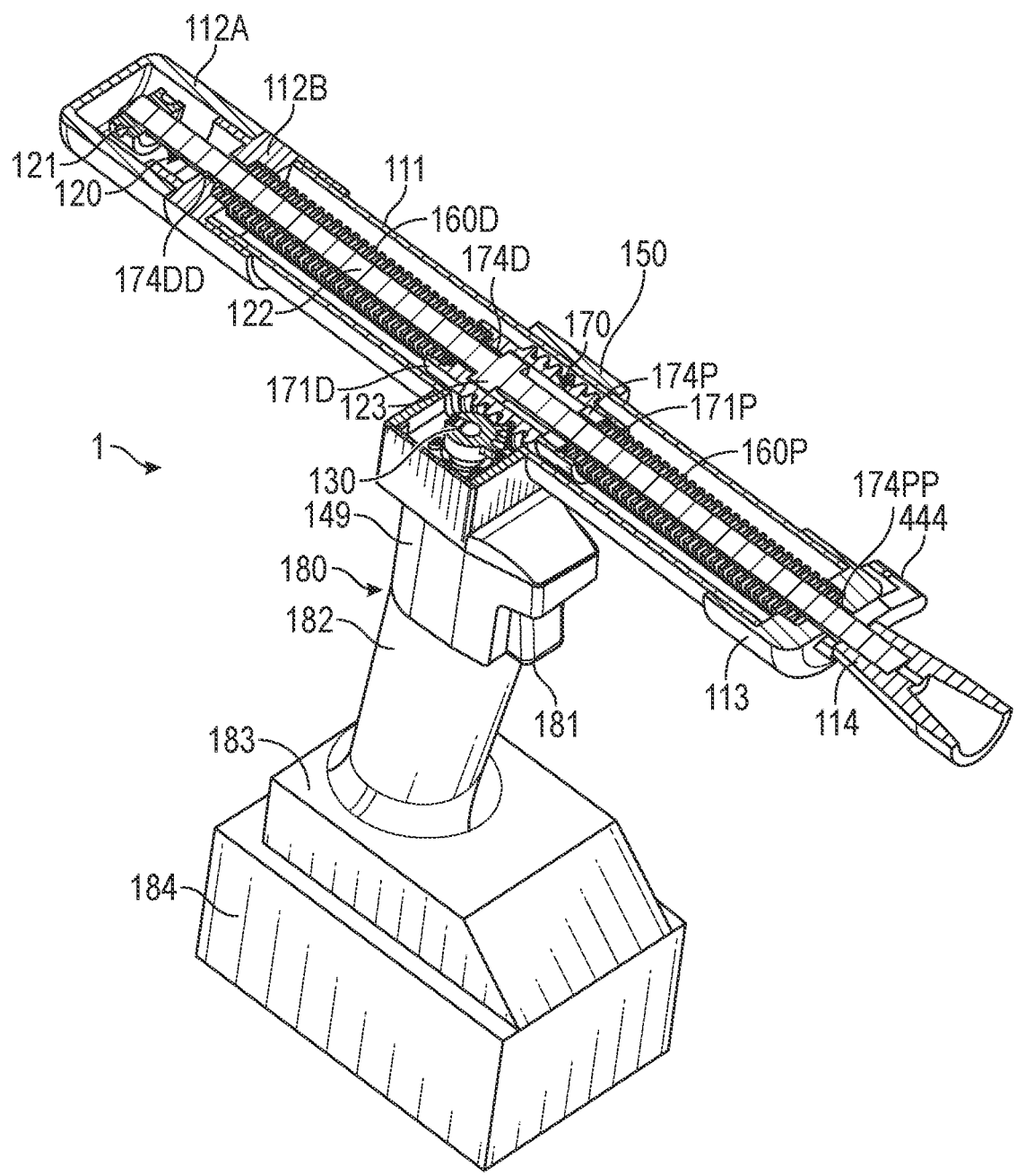
FIG. 2 shows an isometric cutaway view of a bi-spring surgical hammer impact tool consistent with at least one example of this disclosure.
Figure 3:
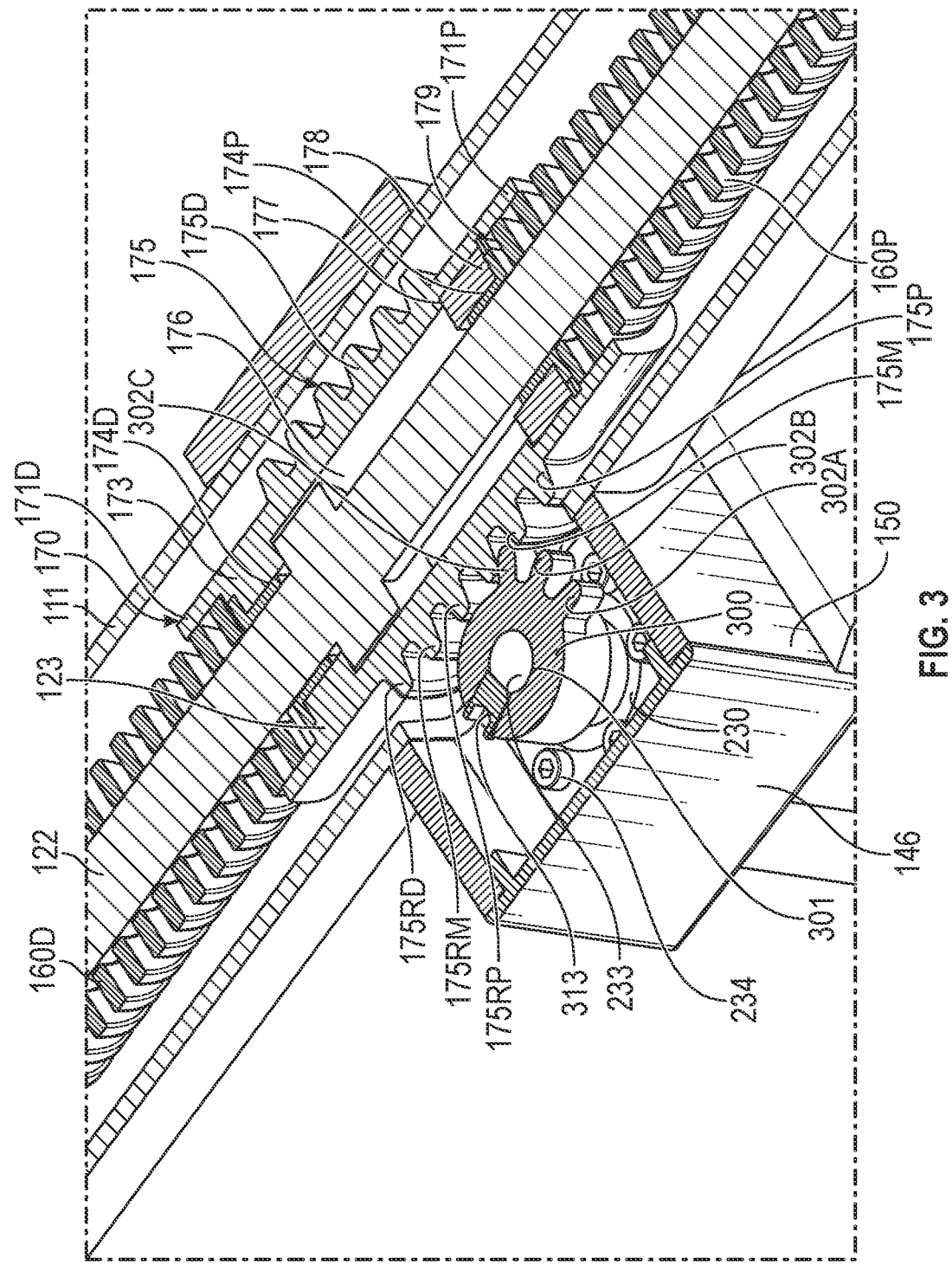
FIG. 3 shows a close-up isometric cutaway view of a bi-spring surgical hammer impact tool consistent with at least one example of this disclosure.

Turning now to the figures, FIG. 1 shows an example of a bi-spring surgical hammer impact tool 1 consistent with at least one example of this disclosure. FIG. 2 shows an isometric cutaway view of the bi-spring surgical hammer impact tool 1 in the neutral position, waiting to be activated. FIG. 3 shows a close up of a region around a motor mounting block 150.

As disclosed herein, bi-spring surgical hammer impact tool 1 can provide a simple, efficient, and robust battery powered handheld bi-spring surgical hammer impact tool for use in surgical procedures. The bi-spring surgical hammer impact tool 1 can include a handle 180 with grip 182 and trigger 181 in an upper handle portion 149. A base 183 of the handle can contain a control circuit and receive a removable and rechargeable battery 184. The top of the handle 180 can connect to the motor mounting block 150. The motor mounting block 150 can contain a mount for the gearmotor 230 (see FIGS. 9 and 10) and the spring and shuttle tube 110.

As shown in FIG. 2, the spring and shuttle tube 110 can include an outer tube 111 that can contain a distal spring 160D, a proximal spring 160P, a shuttle 170, and a driver 120. At the distal end of the spring and shuttle tube 110 can be an end cap 112b that can be connected to a distal end of the outer tube 111, with a cover cap 112A connected to the end cap 112B.

At the proximal end of the outer tube 111 can be an end cap 113. The end cap 113 can include an aperture with a proximal end of the driver 120 extending through the aperture. A tool holder 114 can be attached to the proximal end of the driver 120. The driver 120 can include an elongated drive rod 122. A stop collar 121 can be attached on the distal end of the rod 122. The stop collar 121 can be attached by a clamp-on, screw-on, clip-on, or other connection method. An impact flange 123 can be disposed on a central region of the rod 122. The impact flange 123 can be formed integral with the rod 122 for structural integrity. The tool holder 114 can be attached to the proximal end of the drive rod 122 by threading, for example, so it can be easily changed if needed.

A soft blow clip 444 can be snapped onto the drive rod 122. The soft blow clip 444 can alternatively slide onto the end cap and can allow for several different displacement settings by clicking into place to provide different settings for intensity of impact desired.

As disclosed herein, a rotary sleeve 117 can be disposed in between the end cap 113 and the tool holder 114 and can include an internal shelf 118 disposed on a portion of the rotation and rotate to engage with a mating and similarly restricted shelf 119 disposed on the proximal face of the end cap 113. Helical ramps adjacent to the shelves 118 and 119 can allow the user to access the functionality of the soft blow clip 444 by rotation of the sleeve 117, thereby providing similar displacement(s).

In a neutral state, the distal die spring 160D and proximal die spring 160P can be compressed (i.e., preloaded) to approximately half of their maximum deflection state (e.g., about 45% of their free length). The ends of the springs 160D and 160P can reside in counter bores 171D and 171P in the shuttle 170, respectively, for the distal and proximal spring ends, respectively, that press on the shuttle 170 to maintain their coaxial alignment with the shuttle 170 and the drive rod 122.

The spring 160D and 160P can be die springs that are "coils" and can be made from rectangular cross section material so they tend to provide lateral rigidity to the spring so it is less likely to buckle sideways, which can lead to rubbing (i.e., energy loss and especially when heavily compressed). As disclosed herein, the helical (i.e., coil) springs can rotate slightly when they are compressed. Thus, when two springs are preloaded against the shuttle 170, one of the springs 160D or 160P can be made with a clockwise helix and the other of the springs 160D or 160P can be made with a counterclockwise helix to counteract the rotation of one another and minimize rubbing induced energy losses and wear.

Referring to FIG. 3, the shuttle 170 can have integral annular gear rack drive teeth 175 (e.g., 6 teeth are shown in FIG. 3 with a pitch of 16), which can be offset with respect to the central plane of the shuttle 170 to enable proper fore and aft position for forward and reverse impact. A partial tooth pinion 300 can drivingly engage the shuttle 170. Three annular teeth 175 (e.g., the drive teeth 175P (proximal), 175M (middle), and 175D (distal)) of the shuttle 170 can be used for driving the shuttle 170 forward and three annular teeth (e.g., the retract teeth 175RP, 175RM and 175 RD) can be used for retracting the shuttle 170 forward. An offset from the shuttle 170 center of P/2 can position the distal drive tooth 175D for initial engagement of the tooth 302C of the partial tooth pinion 300 at the start of the process for moving the shuttle 170 to displace the springs 160. However, because only a partial tooth pinion 300 is used, as tooth 302A comes around to re-engage the rack, an additional offset of about P/2 (plus about 1 mm for the 16 pitch gear as disclosed herein) can be used to ensure it does not collide with drive tooth 175M (i.e., the middle drive tooth).

The bi-spring surgical impact tool 1 can use die springs 160D and 160P that can be mounted on either side of the shuttle 170 with integral annular gear rack drive teeth 175. The pitch diameter can be infinite so the flanks of the teeth 175 are not involutes but rather straight. The annular teeth 175 can wrap around the circumference of the shuttle 170 and when a coil spring is compressed, it can rotate slightly. If a conventional section of a gear rack (i.e., straight across and not wrapped annular) were machined into the shuttle 170 (or mounted), as the shuttle 170 compresses the springs (e.g., 160P and 160D), its rotation can cause straight-across teeth 175 to rotate and edge load the drive gear 300 resulting in high contact stresses and early tooth wear. This type of stress loading does not occur on the shuttle 170 with annular gear teeth 175.

The shuttle 170 can be held concentric to the drive rod 122 with distal and proximal sliding contact flanged bearings 174D and 174P, respectively. Once installed and the springs are preloaded to the shuttle 170, the ends of springs 160D and 160P ends can keep the bearings 174D and 174P in place. PEEK can be used as bearing material since it can be dry running in sliding contact and is steam sterilizable. The bearings 174DD and 174PP can center the drive rod 122 in the housing end caps 112b and 113, respectively. The bearings 174D and 174P can center the shuttle 170 on the drive rod 122 during cocking and nominally keep it centered while the shuttle 170 is moving fast to impact the driver 120's center impact flange 123.

As disclosed herein, various elements of the bi-spring surgical impact tool 1 can be collinear and the drive rod 122 can be slender in order to fit down the center of the springs 160 and the shuttle 170. Thus, the mass of the drive rod 122, plus the mass of the tool holder 114 and the tool held therein can be considered the system mass being driven by the impact force from the shuttle 170. Lowering the mass of the drive rod 122 can allow more energy to be transferred to the tool (e.g., a broach). The drive rod 122 can also support the shuttle 170 while it is being cocked, and if the gear tooth separation forces push radially too hard on the drive rod 122 for its size, it can deflect and cause the gear teeth to skip.

In the neutral state, such as just after the driver 120's impact flange 123 has been impacted on its distal side by shuttle 170's distal flange 173, the springs 160 can have oscillated for a few cycles after impact but can have come to rest. For example, 5-10 cycles can occur, which can take on the order of 100-200 milliseconds as the natural frequency of the shuttle 170 is about 40 Hz. The impact can be a mix of elastic and inelastic impacts. A heavier shuttle 170, instead of a lighter shuttle 170, is not necessarily better for energy transfer since a shuttle that is too heavy can cause the speed to be slow, including the time to come to rest, because the natural frequency can be low.

The blows, or impacts, per second required by a surgeon can be in the range of 1-10, and can be selected by the surgeon and controlled by the control circuits in the base 183. The impacts per second can be governed by rotation of the partial tooth pinion 300 by the gearmotor 230. The gearmotor 230 can revolve at a constant rate during the period of use for a set rate of impacts as this allows the gearmotor 230's reflected rotational inertia at the partial tooth pinion 300, which can be considerable, to contribute to the effort to cock the shuttle 170 for another strike, thereby helping with overall system efficiency and increased battery life.

To rotate at a constant speed for a set impact rate, once the last tooth 302A has cleared shuttle proximal drive tooth 175P, the shuttle 170 can be propelled forward by the stored energy in the springs 160D and 160P. As disclosed herein, the two opposed compression springs each of stiffness k both can contribute to the forward energy of the system because they can be preloaded against each other. They can act as one with bidirectional stiffness 2 k as long as they are preloaded against each other. Meanwhile, as the shuttle 170 is accelerating forward increasing its kinetic energy as it is transferred to the shuttle 170 from the stored potential energy in the springs 160D and 160P, the partial tooth pinion 300 can continue to rotate. The shuttle 170 can impact the driver 120 and settle down in time for partial tooth pinion tooth 302C to have come around and make contact with shuttle distal drive tooth 175D as shown in FIGS. 2 and 3.

Figure 4:
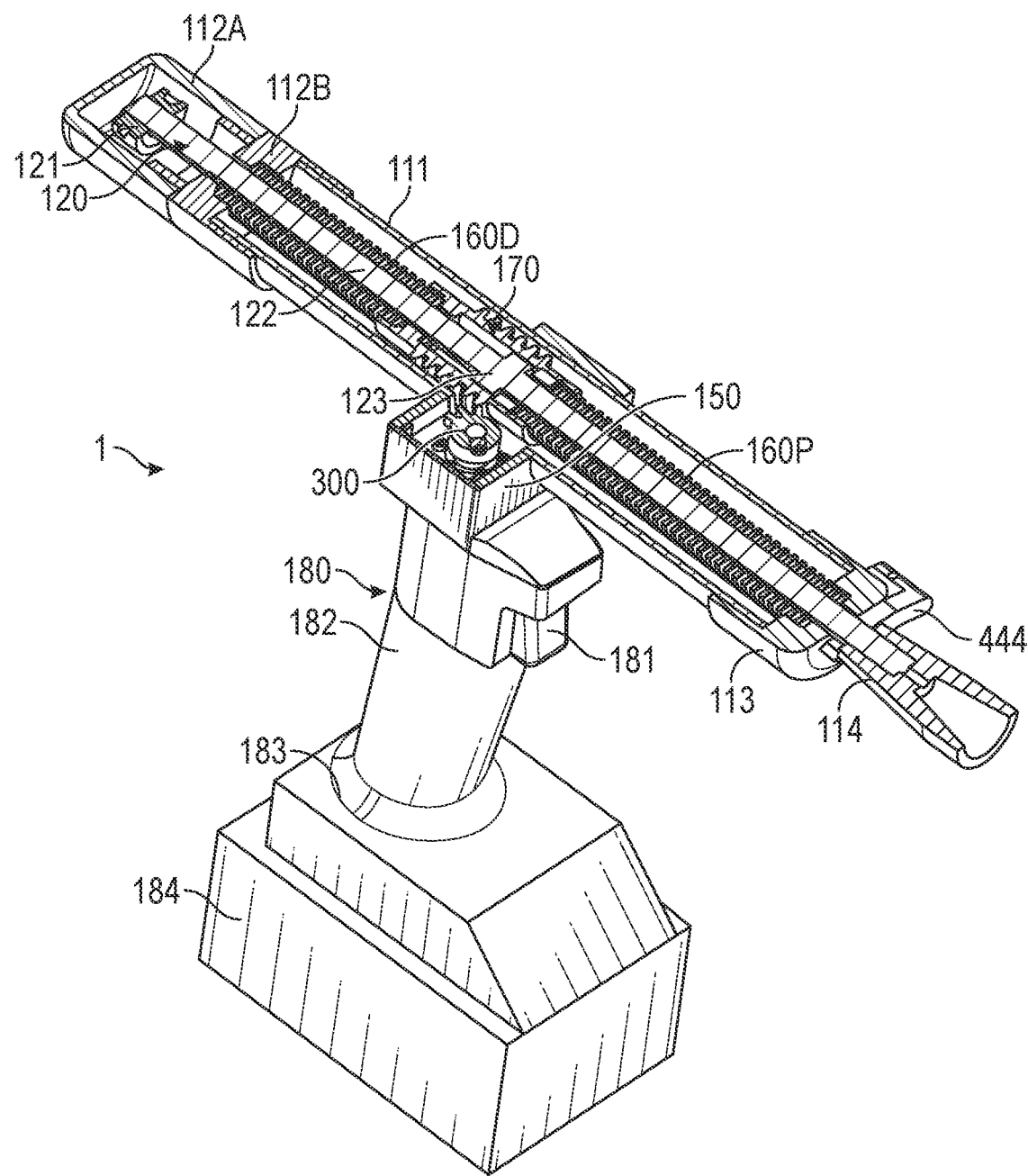
FIG. 4 shows an isometric cutaway view of a bi-spring surgical hammer impact tool consistent with at least one example of this disclosure.
Figure 5:
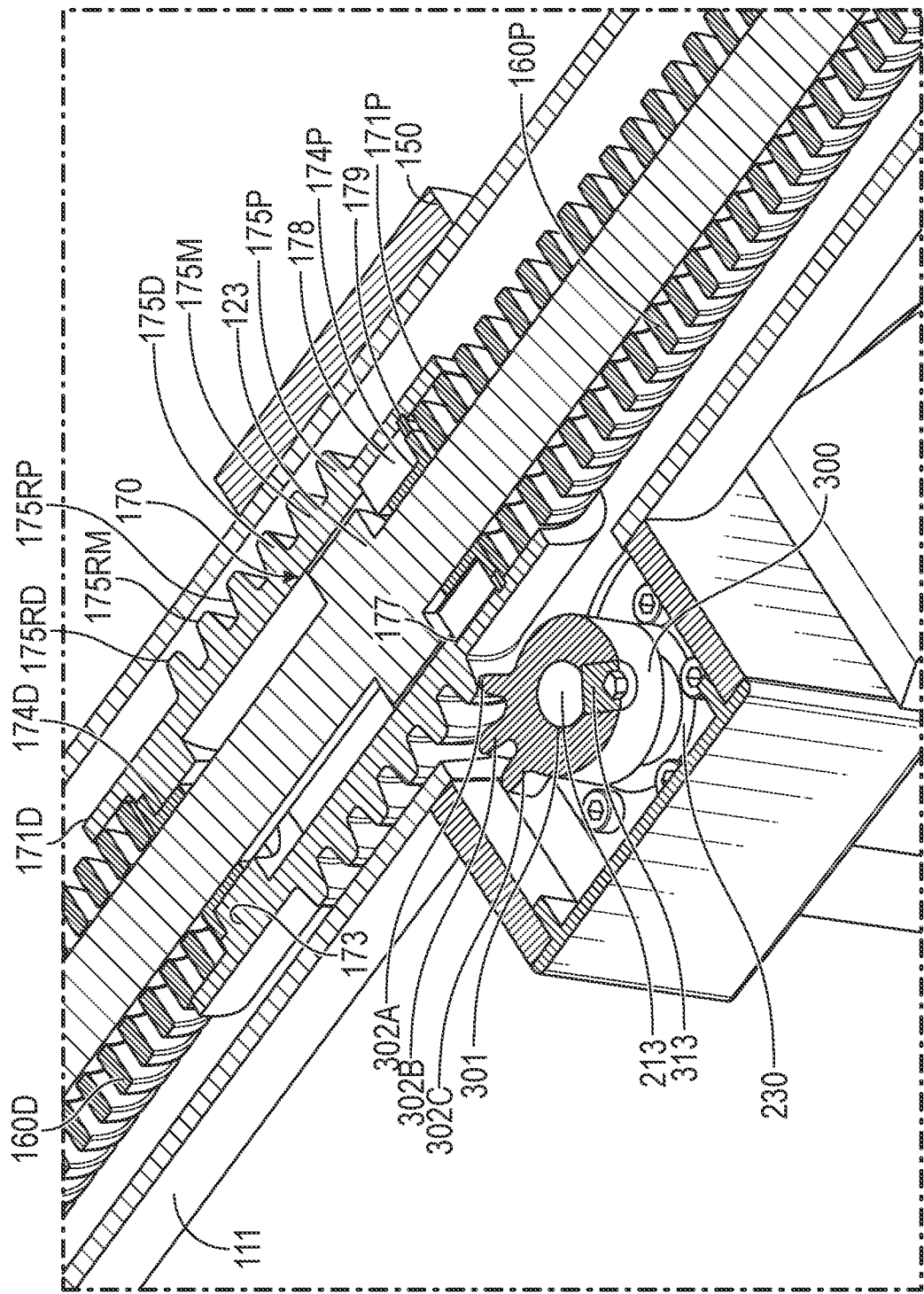
FIG. 5 shows a close-up isometric cutaway view of a bi-spring surgical hammer impact tool consistent with at least one example of this disclosure.
Figure 16A:
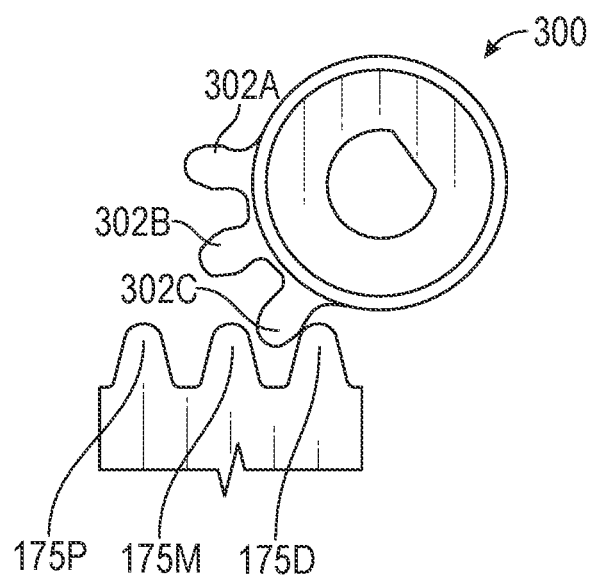
FIGS. 16A, 16B, and 16C show multiple different stages of engagement of a partial tooth pinion and shuttle gear teeth consistent with at least one example of this disclosure.
Figure 16B:
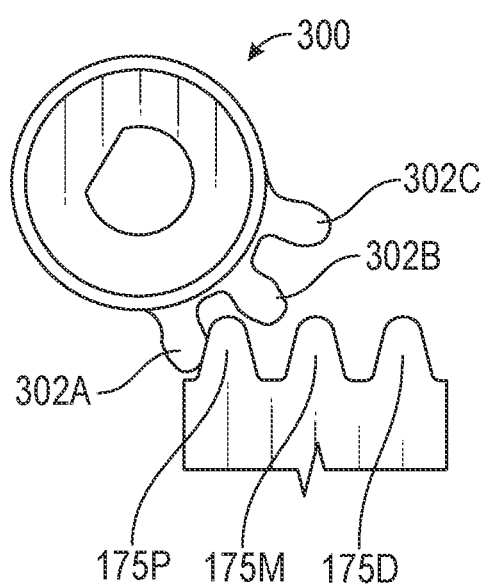
Figure 16C:
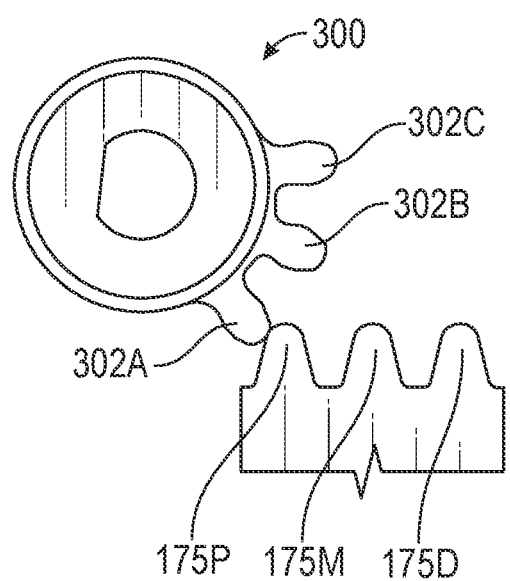

For full strength forward impact, the user can push the bi-spring surgical impact tool 1 forward such that the soft blow clip 444 (or another spacer embodiment) is pressed against the proximal surface of the end cap 113, which can displace the driver 120's impact flange 123 backwards. Its distal face can then be pressed against the proximal face of the shuttle 170's impact flange 173. At this point the partial tooth pinion tooth 302C can engage shuttle distal drive tooth 175D and turning counterclockwise as shown can move the shuttle 170 back to the ready-to-fire position shown in FIGS. 4 and 5. FIG. 16 shows the progression of steps from initial making of tooth contact (a), to the end of rolling contact between the involute teeth (b), to the final displaced position where tooth 302A breaks contact with shuttle proximal drive tooth 175P.

Rotation of the partial toot pinion 300 from initial contact to final moment of rolling can cause linear motion of the rack. There can be additional motion until tooth 302A breaks contact with shuttle drive tooth 175P and the shuttle 170 is thus released and accelerates towards the driver 120's impact flange 123. During this period of motion, there can be sliding contact between tooth 302A and 175P. If finer resolution of motion is desired, a finer pitch can be used but this may cause the teeth to be smaller and weaker.

The gear teeth base material (e.g., 175 and 302) can be hardened, ground with tips rounded, and coated with a wear resistant coating, such as tungsten carbide applied by physical vapor deposition. As the teeth are not large with respect to depth of contact stresses, they can be typically be through hardened. A dry laminar solid lubricant can also be applied during the coating process, one such as tungsten disulfide $WS_2$, a soft lamellar material similar to graphite/$MoS_2$. Also note that since the coating can have a much higher modulus of elasticity and strength than the base steel of the gear, the contact stress can be limited by that of the steel, for if the steel should yield below the coating layer thickness, the coating can peel off. In a gear with full circumference of teeth engaging another gear with full circumference of teeth, the tooth tip edge does not make high stress contact and thus is generally not rounded over; yet here the last tooth's tip can make high force contact with the rack teeth just before firing. This tooth tip edge to edge contact is like the edges of a trigger system, and thus care is needed to prevent unacceptable wear.

Driver 120's impact flange 123 can be impacted on its distal face to produce force in the forward (proximal) direction for driving a tool (e.g., a rasp or broach) into an object (e.g., a femur or humerus) by distal drive flange 173's proximal face. The distal drive flange 173 can be integrally made with the shuttle 170 as it can be subject to the highest stresses. Note that the distal spring 160D can be coaxial with the driver 120 and the flange 123 and thus force can be applied directly to the opposite side of the flange that impacts the driver flange 123 thereby making a robust design.

Figure 6:
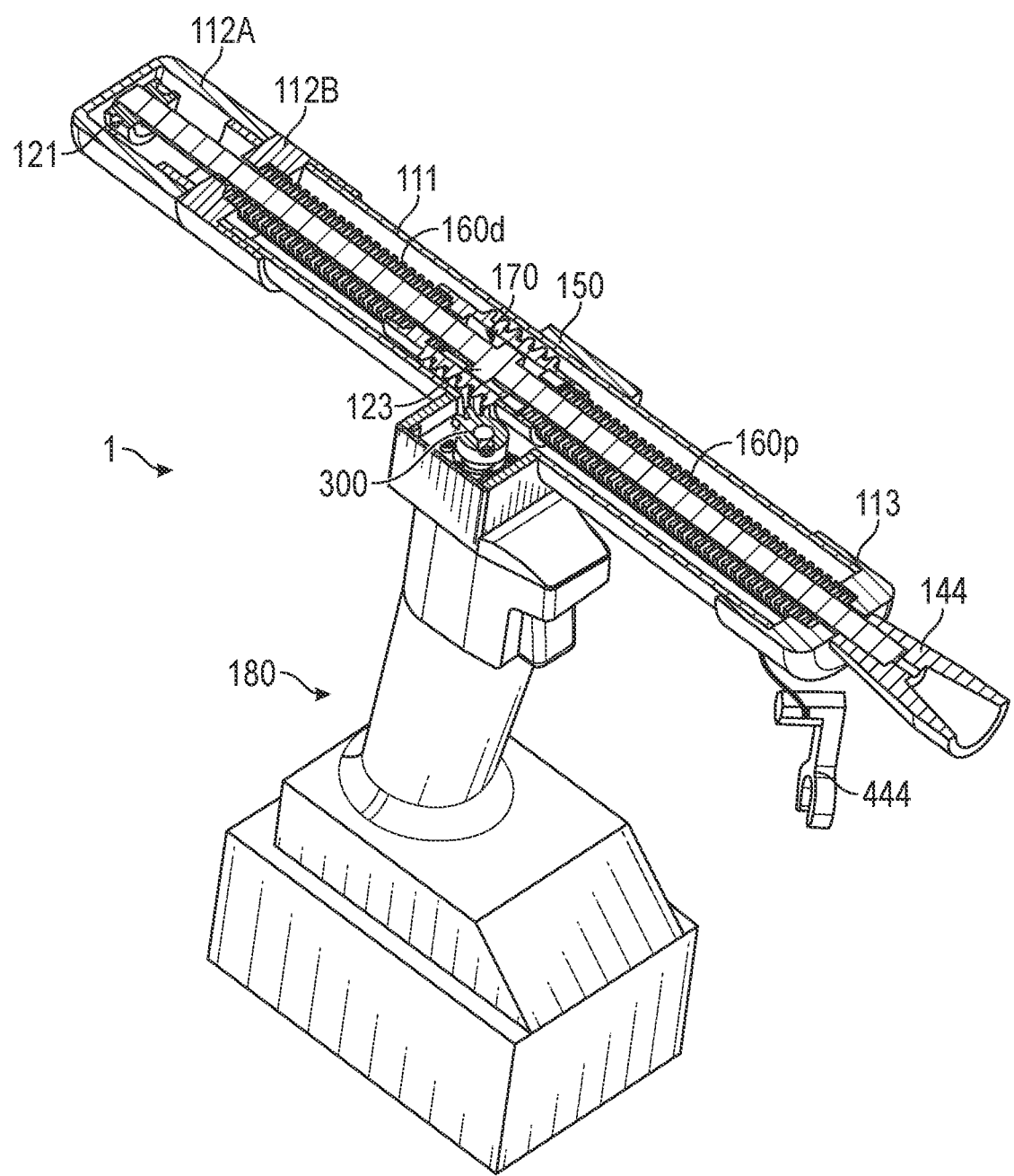
FIG. 6 shows an isometric cutaway view of a bi-spring surgical hammer impact tool consistent with at least one example of this disclosure.
Figure 7:
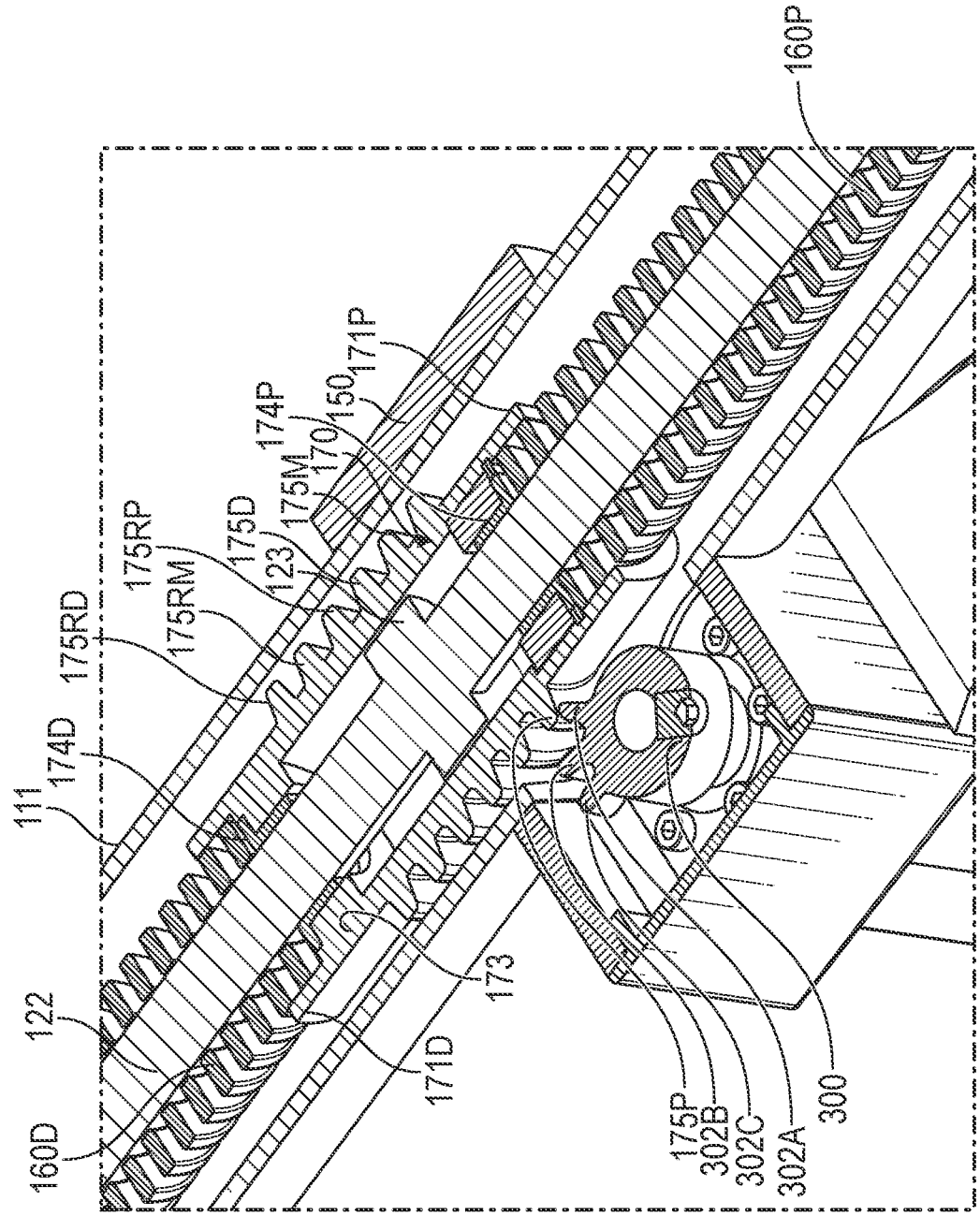
FIG. 7 shows a close-up isometric cutaway view of a bi-spring surgical hammer impact tool consistent with at least one example of this disclosure.
Figure 12:
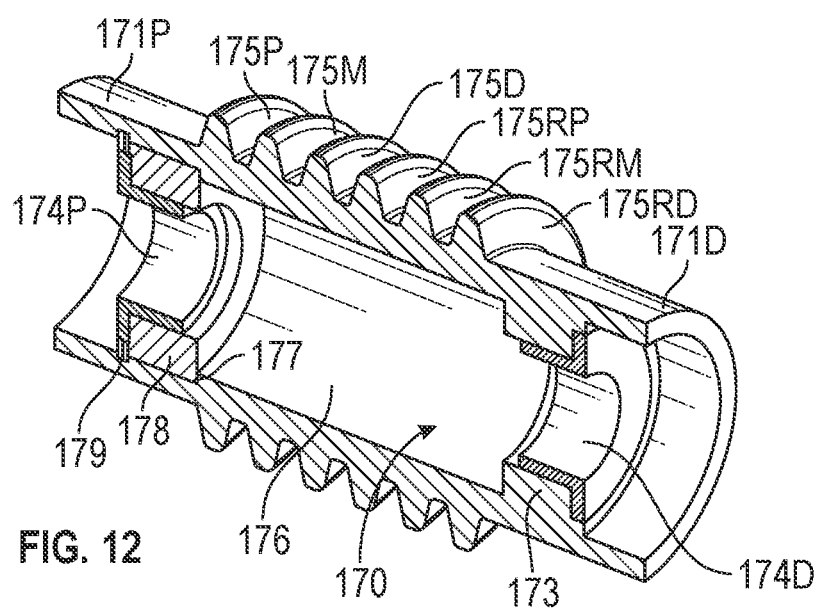
FIG. 12 shows a cross-sectional isometric view of a shuttle consistent with at least one example of this disclosure.
Figure 13:
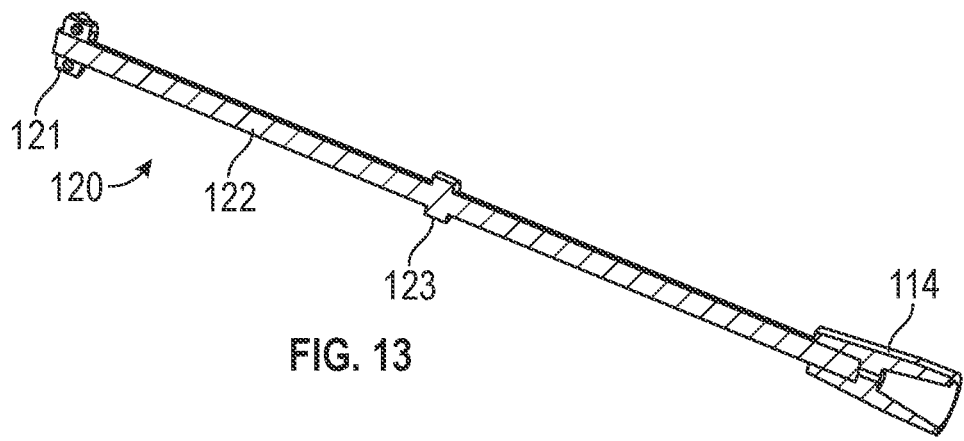
FIG. 13 shows a cross-sectional isometric view of a drive rod subassembly consistent with at least one example of this disclosure.
Figure 14:
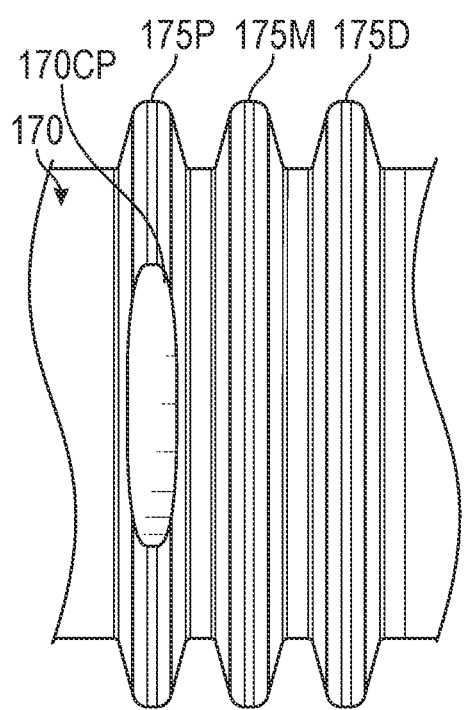
FIG. 14 shows a contact radius of a shuttle member's circular gear rack consistent with at least one example of this disclosure.
Figure 15:
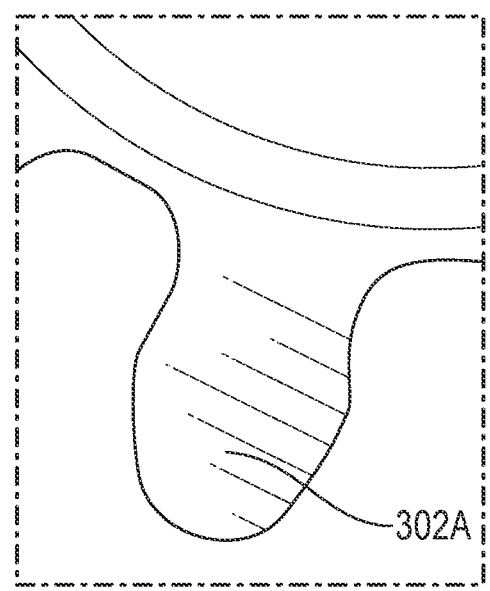
FIG. 15 shows a contact radius of a drive gear tooth consistent with at least one example of this disclosure.

For retraction of the driver 120, as shown in FIGS. 6 and 7 (and see FIGS. 2 and 12 for the shuttle's 170 components), the flange insert 178, which can be seated against counterbore face 177 in the shuttle 170's proximal end, can be held in place with internal snap ring 179. In the retract mode the force does not have to be as high. This can be adjusted at assembly by making the driver 120's end clamp on stop collar 121 closer to the impact flange 123 (see FIG. 13).

Figure 8:
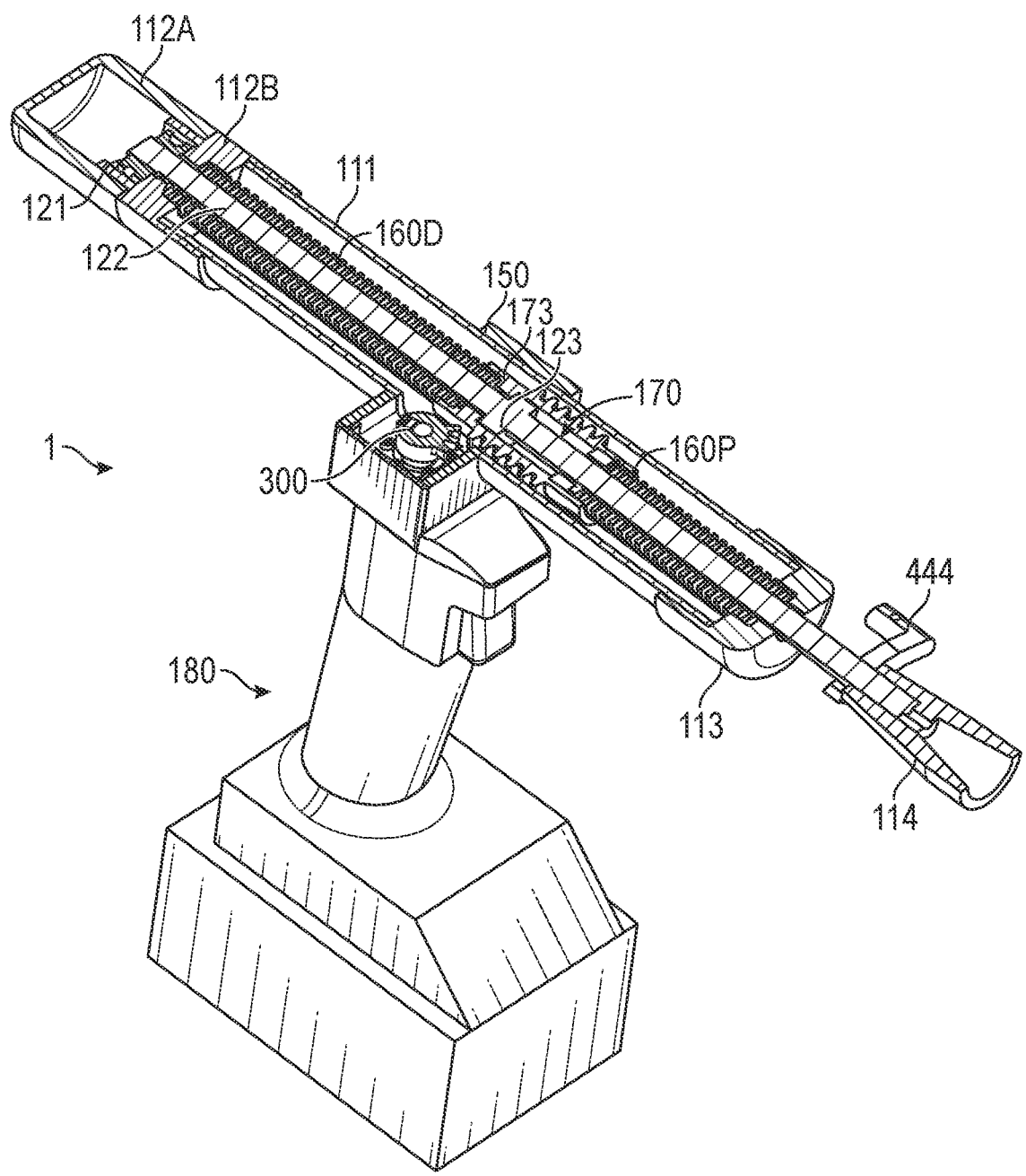
FIG. 8 shows an isometric cutaway view of a bi-spring surgical hammer impact tool consistent with at least one example of this disclosure.

For rearward impact to extract a tool, the user can pull the bi-spring surgical impact tool 1 backwards such that stop end collar 121 is pressed against the counterbore in end cap 112B and the proximal surface of the driver 120's impact flange 123 faces the distal surface of the shuttle's flange insert 178. Selecting reverse (e.g., by a reverse button on the handle 180) and activating the gearmotor 230 (e.g., with switch 181 on the handle 180), the partial tooth pinion 300 can rotate in the opposite direction for that of forward impact. The rotation can cause the partial tooth pinion tooth 302A to engage shuttle 170's proximal retract tooth 175RP and turning clockwise as shown, can move the shuttle 170 forward to the ready-to-fire position, shown in FIG. 8, until tooth 302C breaks contact with shuttle 170's distal retract tooth 175RD. Upon breaking contact, the springs 160 can move the shuttle 170 rearward at high speed until the driver's impact flange 123 proximal surface is impacted by distal surface of the shuttle's flange insert 178.

The shuttle 170 can have three teeth for retraction, 175RP, 175RM, and 175RD (proximal, middle, and distal retract teeth respectively), each in this embodiment that are engaged by the three teeth on the partial tooth pinion 300. Note that due to the offset of the teeth for forward impacting of the tool, because of there being still just three teeth on the partial tooth pinion 300, the rearward (pull out) energy can be about 30% less than the forward energy. However, this is adequate as it takes less force to pull out a broach, for example, than to drive it into bone.

Figure 11:
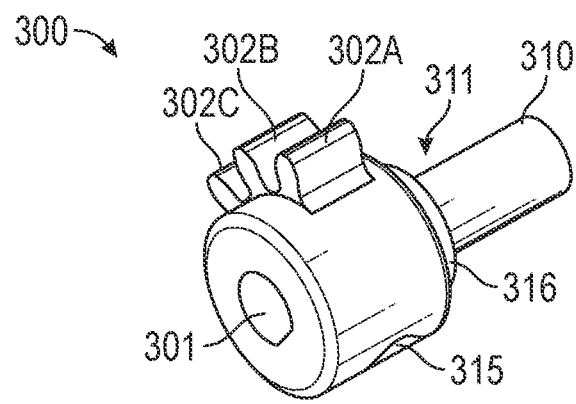
FIG. 11 shows an isometric view of a partial tooth pinion consistent with at least one example of this disclosure.

The shuttle 170's circular gear rack drive teeth 175 can be driven by teeth 302 on the partial tooth pinion 300 (see FIG. 11) which can have a D-shape bore 301 to sliding fit onto the gear motor's D-shaped output shaft 233. In FIG. 3 only the front flange of the gearmotor 230 can be seen, but one of the bolts 234 that hold it in place is shown. A flat tip setscrew 313 can hold partial tooth pinion 300 in place although as will be discussed, the partial tooth pinion 300 can be axially constrained by the gearmotor shaft and outrigger support bearings (see FIG. 9). As disclosed herein, three teeth, 302A, 302B, and 302C as determined by the gear pitch and pitch diameter are needed to drive the rack the desired distance in either direction.

The rear collar 121 on rod 122 can be a fixed C-clamp collar, but to adjust the retraction force, it can be a threaded collar on the shaft so the surgeon can rotate the collar and adjust its axial position with respect to flange 123. In this case, the read cap 112A can be removable or the threaded collar having a protrusion through it for dialing the position.

In forward and reverse impacts, the energy can be changed by changing the distance the shuttle travels (i.e., accelerates) before it impacts the flange 123. Thus, the spring stiffness (e.g., spring size) can be fixed to the maximum of what may ever be needs, and with sensitivity the energy achieved per blow can be easily adjusted by changing the position of the flange 123 inside the shuttle cavity 176. This can enable great robustness of design, as it is not a slip clutch or other energy robbing element.

Motor gearbox combinations ("gearmotor"), particularly those with high ratios, can output very high torques. Often this torque can be transmitted to another shaft with a coupling element. Sometimes a gear or pulley can be directly attached to the gearmotor output shaft. However, as disclosed herein, there can be a shock load of the load on the drive gear (e.g., the partial tooth pinion 300) suddenly being released and it may be found that the equivalent radial load of the torque transmitted divided by the pitch radius of the gear exceeds the allowable radial load on the gearmotor 230 output shaft 233. As the gear is moved out along the shaft 233, the problem can be exacerbated.

Figure 9:
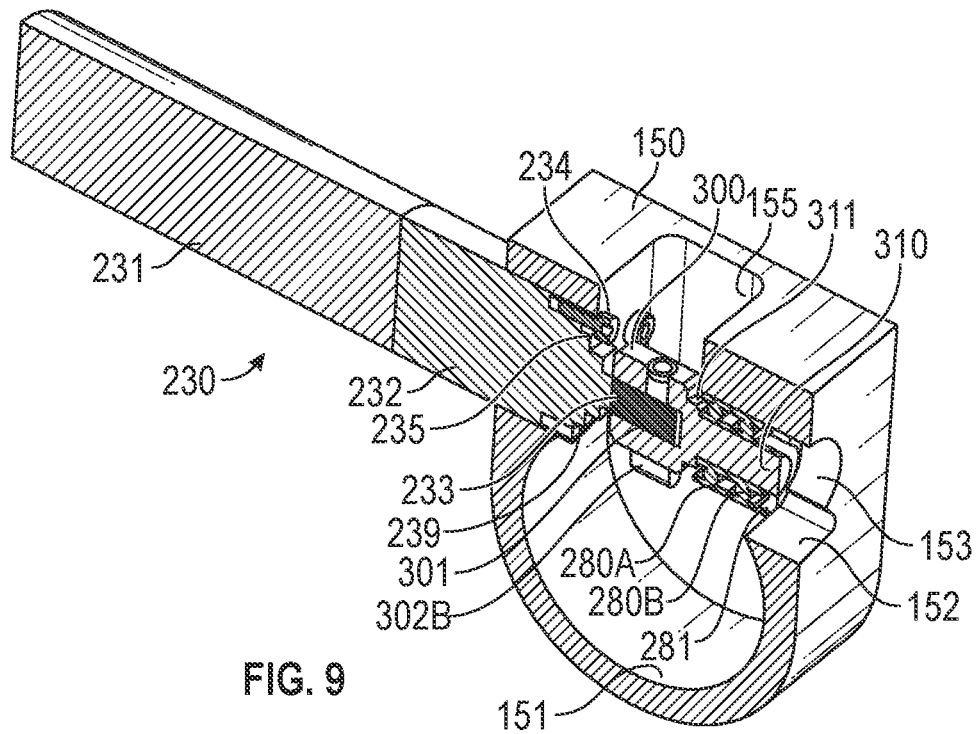
FIG. 9 shows a cutaway isometric view of a gear motor housing subassembly consistent with at least one example of this disclosure.
Figure 10:
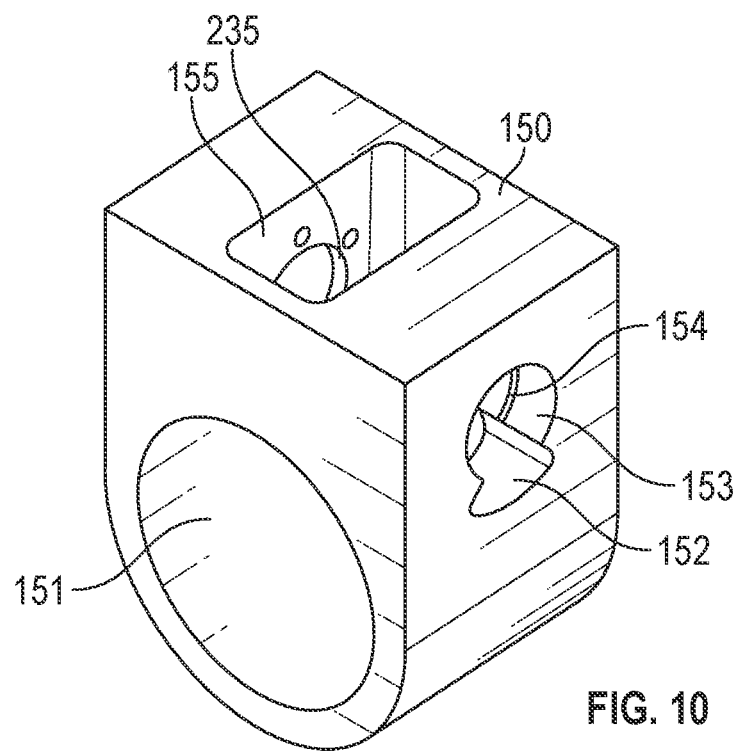
FIG. 10 shows a cutaway isometric view of a gear motor housing consistent with at least one example of this disclosure.

A solution to this problem, as shown in FIGS. 9 and 10, can be a monolithic motor mounting block 150. High quality gearmotors front faces can, have a precision round locating boss which can be concentric with their inner bearings that support the output shaft 233. Hence, they can be mounted such that the boss can be a sliding fit in a precision bore 153 that can extend across the region in which the shuttle 170 passes to the other side of the motor mounting block 150 where precision outrigger support bearing(s) 280 can be placed. The bore diameter for the locating boss can be the same as the bore 153 required for the outrigger bearing 280, so a straight through line bore operation can be made and the hole reamed to tolerances. Alignment can thus be to within 10 microns without great effort.

In the center region of the structure into which the precision bore 153 has been made, a cavity can be made that contains the partial tooth pinion 300 on an integrally formed gear shaft structure 311. On this gear shaft structure 311, on the gear end (e.g., the partial tooth pinion 300), the diameter can be big enough for a precision bore to mate with the gearmotor shaft 233, including a shaft feature such as a flat, keyway or spline so torque transmission can be obtained without the need for a coupling. The other end of shaft structure 311 can have a shaft 310 that fits into the outrigger bearing(s) 280. Two bearings 280 can be used to give some additional moment support and stiffness. The effect can be a supported shaft (e.g., the structure 311) with a gear (e.g., the partial tooth pinion 300) in the middle and the radial load from the gear teeth (302B) tangential force, as well as gear tooth separation forces, can be shared by the gearmotor shaft support bearings and the outrigger bearings 280. Precision fits and alignment can be obtained by this arrangement, which is made possible by the monolithic structure of the motor mounting block 150.

As shown in FIGS. 9 and 10, since the gear tooth tangential and separation forces always essentially add to have a net upwards direction, the outrigger bearings' bore 153 can have its lower quadrant relieved to form a fan-shaped access 152 enable the partial tooth gear 300 to be slid into place. A snap ring groove 154 in the bore 153 can hold a snap ring 281 to axially retain the bearings in the bore 153, which would be covered in the fully assembled device by cap 145 (see FIG. 1). A top access port 155 can allow access to tighten bolts 234 to hold the gearmotor 230's gearhead 232 securely to the housing 149. This access port can be covered in the fully assembled device by cap 146 (see FIG. 1). The bore 235 can be collinear and same diameter as bore 153 so they can be line-bored for high precision. Hence, the gearmotor front boss 239 can be precisely held concentric as discussed above and it is tolleranced by the manufacturer for precise alignment of the gearmotor 230. By selecting outrigger bearings 280A and 280B to have the same outside diameter as the boss 239, precise alignment on the order of ten microns, is possible so when the partial tooth pinion shaft 310 fits in the bearings' 280 bores, and the partial tooth pinion D-shape bore 301 slides over the gearmotor shaft 233, the bearings in the gearmotor 230 will not be over constrained by the outrigger bearings 280a and 280b, which seat against shaft 310's shoulder 316. As a result, high radial loads due to tangential and gear tooth separation forces on the gear teeth, 302, can be shared by the bearings in the gearmotor 230 and the outrigger bearings 280.

In the case of the circular gear rack teeth 175 disclosed herein, the crown of the gear rack tooth means there will not be misalignment. Note that this crowning can result in higher contact stresses than a conventional flat flank gear rack tooth engaging with a drive gear would experience, but this can be engineered as disclosed herein with analysis of the system that includes not only calculation of the gear tooth strength but also of the contact stress of the drive gear teeth 302 with the circular gear rack teeth 175.

The length dimensions of the elements allow for the energy stored in a mechanical coil-type spring to vary with the square of the compression of the spring. Hence one starts with the compressed and free lengths of the springs. The compressed length of the spring is not the solid height of the spring, as this can result in too highly stressing the springs with repeated compressions.

Hence the calculation of the length of the drive rod 122 can ensure that when the user pushes on the tool, the rear face of the tool holder 114, which is attached to the end of drive rod 122, comes into contact with the front of the system's outer tube 111 front end cap 113. The center impact flange 123 of the drive rod 120 can be positioned within the system such that as when the shuttle 170 is cocked, its proximal flange (e.g., nearest the tool holder 114) inner face is just in contact, or a tolerance clearance of about one mm to prevent an over constraint condition where the drive gear 300 has just a little bit more to go before it can release and fire the shuttle 170, but the drive rod 122 impact flange 123 is already in contact with the shuttle 170's proximal flange inner surface.

Figure 17:
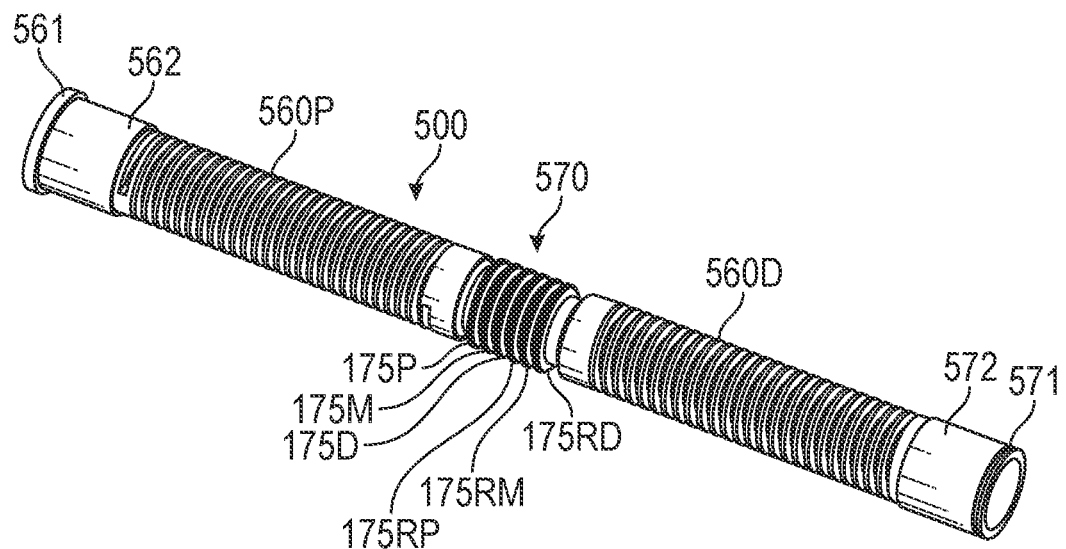
FIG. 17 shows an isometric view of a monolithic machined spring and shuttle consistent with at least one example of this disclosure.
Figure 18:
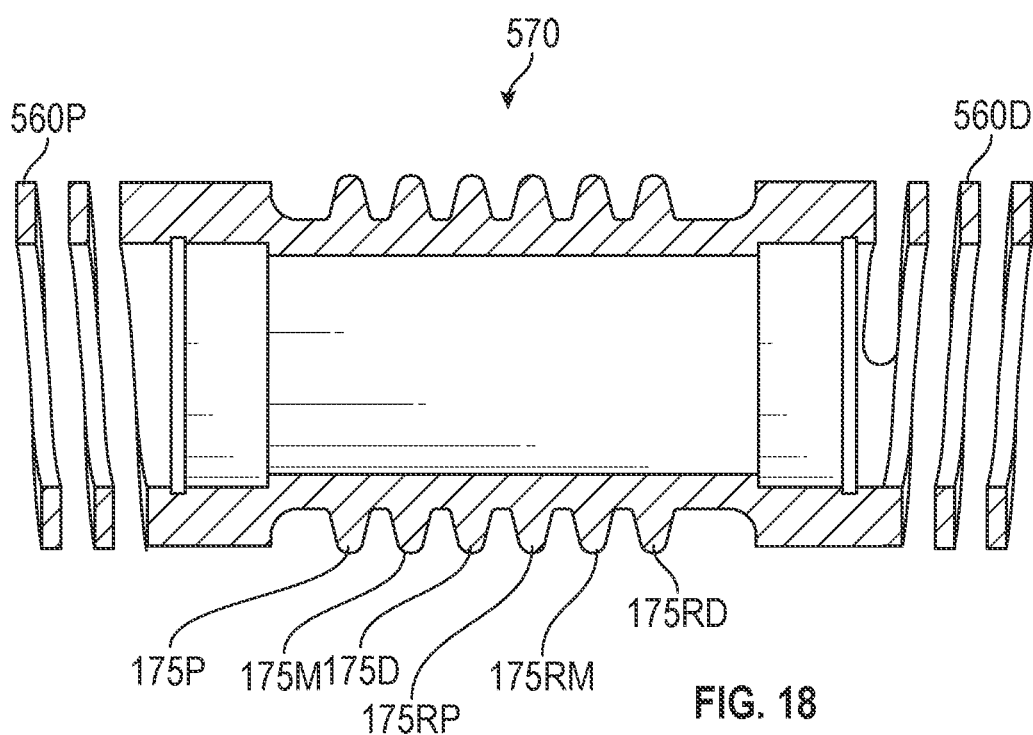
FIG. 18 shows a cross-sectional view through a center region of a monolithic machined bi-spring and shuttle consistent with at least one example of this disclosure.

FIGS. 17 and 18 show a monolithic spring shuttle structure 500 that can include the two springs 560P and 560D and the shuttle section 570 with integral gear teeth. The springs can be machined with 560P being clockwise (CW) and 560D being counterclockwise (CCW). It can be made integral by machining the springs from a steel rod or tube. The circular rack teeth 175 can be machined into shuttle section 570. The forward impact surface for driving the tool forward can be monolithic with the shuttle 500, but a high force capacity snap ring could be used as well. A custom machined spring can provide an advantage by having a larger diameter and somewhat shorter spring can be used, which can also incorporate the end caps needed to mate with the spring and shuttle tube 110. In this instance, one spring 560 can be clockwise and one can be machined counterclockwise, so there is no net appreciable torque on the ends that attach to the outer tube 111. Thus, sliding or wear can be avoided and/or reduced. Preload can be obtained when the system's outer tube 111 is placed over shuttle 500 and then the proximal end of the tube seats against the flange 561. Shuttle 500 can be gripped from the inside (e.g., with an expansion tool) and pulled in tension until a snap ring can be fitted into the groove 571. The shuttle 500 can be kept centered in the outer housing tube 111 by end bosses 562 and 572, which can be about 2-3 mm larger in diameter than the outside diameter of the circular rack gears 175P, 175M, 175D, 175RP, 175RM and 175RD for forward (i.e., drive) and rearward (i.e., retract) impact actuation of the shuttle section 570.

As disclosed herein, the bi-spring surgical impact tool 1 can be designed to apply about 6 Hz impacts with a maximum of about 4 joules per impact. The soft blow clip 444 as disclosed in FIGS. 1, 2, 4, and 6 can provide a simple force control mechanism that can lower impact force by reducing the effective travel of the drive springs.

Figure 19:
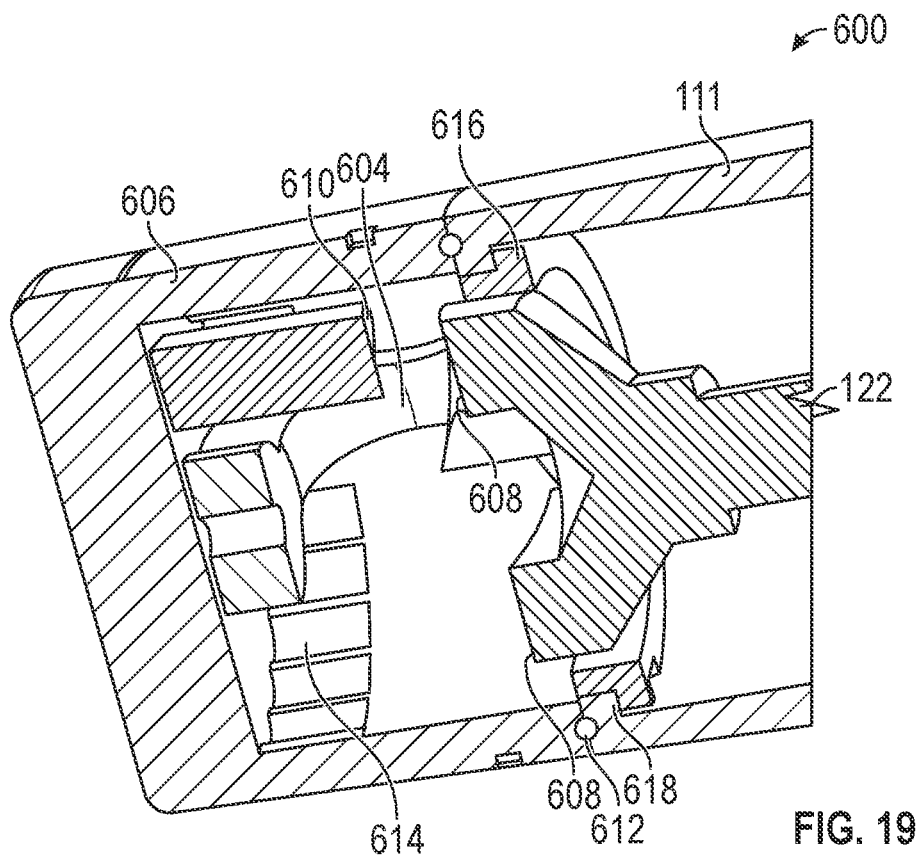
FIG. 19 shows a cutaway perspective view of a force control mechanism of a bi-spring surgical hammer impact tool consistent with at least one example of this disclosure.
Figure 20:
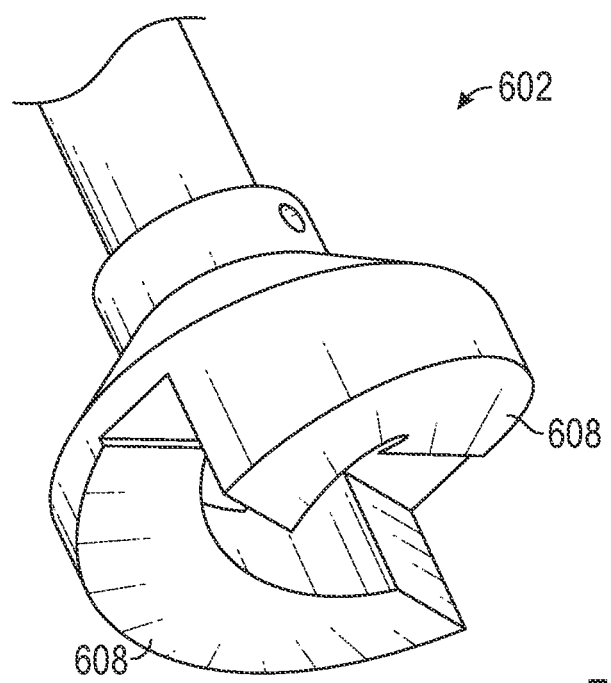
FIG. 20 shows a perspective view of a shaft helix of a force control mechanism of a bi-spring surgical hammer impact tool consistent with at least one example of this disclosure.
Figure 21:
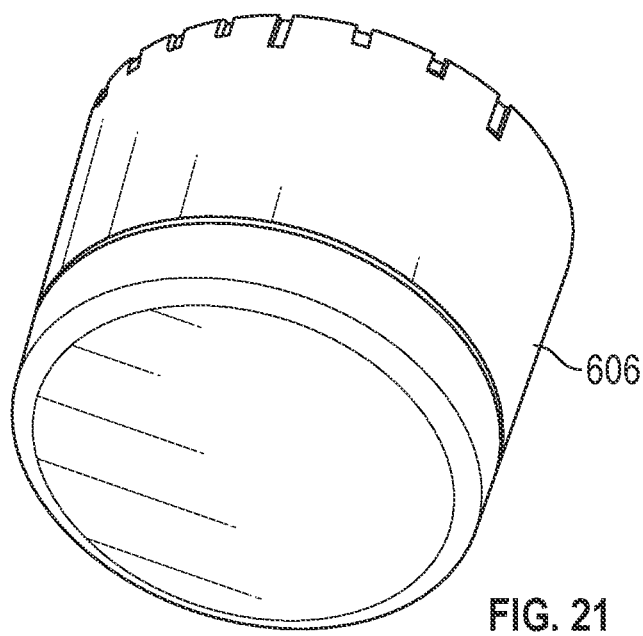
FIG. 21 shows a perspective view of a handle of a force control mechanism of a bi-spring surgical hammer impact tool consistent with at least one example of this disclosure.

With reference to FIG. 19, a continuously variable force control mechanism 600 can include a shaft helix 602 and a yoke 604 received in a handle 606 (FIG. 21) that can be mounted on a rear end of the outer tube 111 in place of the end cap 112A. The shaft helix 602 can be attached to the back of the drive shaft 122 (such as by set screws) that can be fixed against rotation. The shaft helix 602, as shown in FIG. 20, can include a pair of helixes 608 each having a helical face that interacts with the force control handle 606. The use of two helixes 608 can eliminate lateral loading on the drive shaft during impact with mating helix(es). The range of the impact force delivered by the bi-spring surgical impact tool 1 can be determined by the slope of the helixes 608 and degree of rotation of the handle 606. To provide a chosen geometry of 50% of maximum force, the helix can rise 6 mm over 112 degrees of rotation, although other designs can be implemented with a different rise amount.

Figure 22:
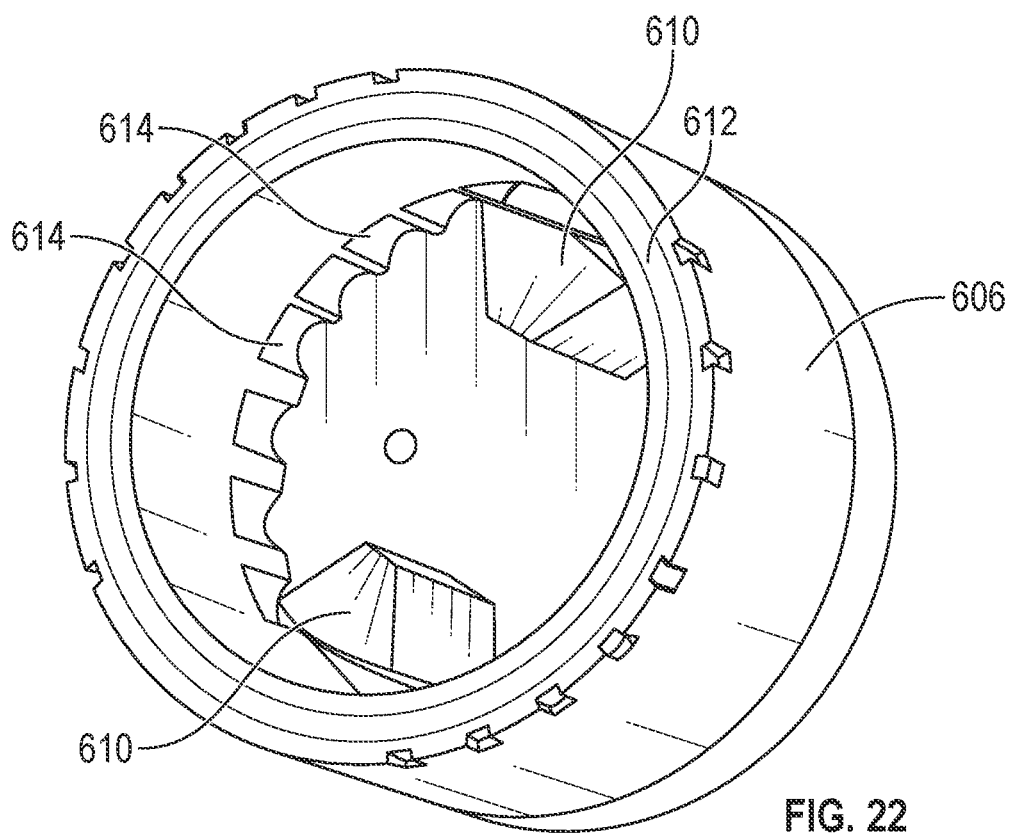
FIG. 22 shows an internal perspective view of a handle of a force control mechanism of a bi-spring surgical hammer impact tool consistent with at least one example of this disclosure.

As shown in FIG. 22, the handle 606 can include a pair of mating helixes 610 on the interior of the handle 606 that mate with the helixes 608 of the shaft helix 602. Rotating the handle 606 can displace the driveshaft 122 forward, reducing the travel of the driveshaft 122 prior to impact by the shuttle 170 against the impact flange 123 and thereby reducing the force transmitted to the tool head. This means the control handle 606 can be subject to a fraction of loading during impact. An O-ring 612 can be disposed along a front edge of the handle 606, near the circumference, sealing the force control mechanism 600 for autoclavability. The O-ring 612 can also provide damping and frictional torque opposing impact displacement. Detents 614 can be provided on an inner surface of the handle 606, proximate to the outer circumference.

Figure 23:
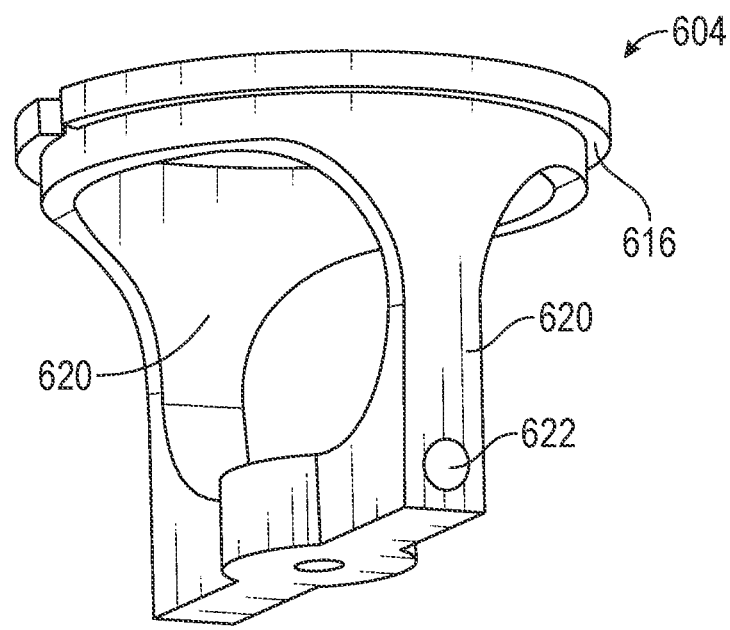
FIG. 23 shows a perspective view of a yoke of a force control mechanism of a bi-spring surgical hammer impact tool consistent with at least one example of this disclosure.
Figure 24:
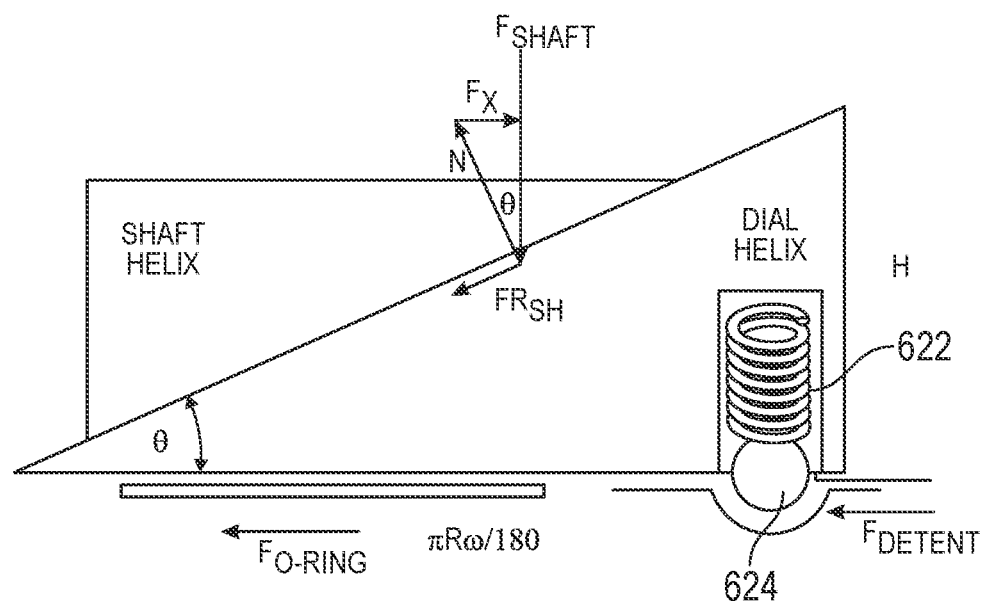
FIG. 24 shows a force analysis diagram for a force control mechanism consistent with at least one example of this disclosure

As shown in FIG. 19, the yoke 604 can include a flange 616 that extends beyond the handle 606 and seats against a mating flange 618 in the outer tube 111. As shown in FIG. 23, the yoke can include an arm structure 620 that extends into the handle 606 and can include an aperture 622 for supporting a spring-loaded ball bearing 624 as shown in FIG. 24. The yoke 604 can be fixed relative to the outer tube 111 and the spring-loaded ball bearing 624 can interact with the detents 614 in the interior of the handle 606. The yoke 604 can provide attachment for the handle 606 to the outer tube 111.

With reference to FIG. 24, the generalized relationship between the shaft impact force and variables involved in maintaining a desired force control setting are discussed. In FIG. 24, the helixes 608 can be treated as two-dimensional inclines, with a height, H, and base equal to the displacement distance of the helix 608 circumference $\pi R\omega/180$, where R is the radius (measured to the average radial center of contact of the helixes) and $\omega$ is the rotation of the handle, measured in degrees.

Other elements in the system can include the O-ring 612 and the spring-loaded ball bearing detents 614/624 that can maintain the force setting the surgeon desires under the 6 Hz impacts of the tool.

Referencing FIG. 24, the sum of the forces in the x-axis: the radial force generated by shaft impact can be opposed by the forces of: 1) the internal friction of the helices, 2) the friction imposed by the O-ring, and 3) the force required to displace the ball bearing detent 614/624, summarized as:

$$\Sigma(x): F_{shaft}(x) = F_{o\text{-}ring} + F_{helix} + F_{detent} \quad \text{Equation 1}$$

Analyzing each term separately:

$$F_{shaft(x)} = F_{shaft} \sin\Theta = F_{shaft} * 180H/\pi R\omega \quad \text{Equation 2}$$

$$F_{o\text{-}ring} = \mu_{o\text{-}ring} F_{shaft} \quad \text{Equation 3}$$

$$F_{helix} = (X \text{ component of friction}) = N_{\mu helix} \cos\Theta \quad \text{Equation 4}$$

$F_{detent}$ can require evaluation of the detent.

Figure 25:
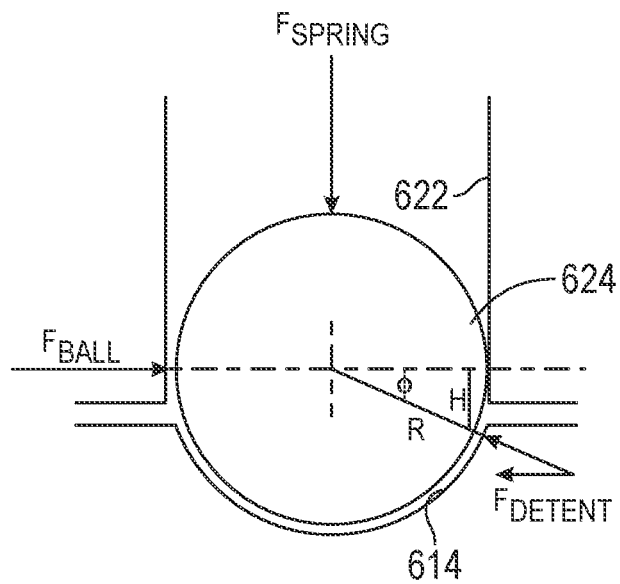
FIG. 25 shows force analysis diagram of a ball bearing detent consistent with at least one example of this disclosure.

With references to FIG. 25, to find $F_{detent}$, a temporary internal variable $F_{ball}$, can be introduced where $$F_{ball} = \text{force on ball} = F_{shaft}(x) - F_{o\text{-}ring} - F_{helix} \quad \text{Equation 5}$$

A torque analysis shows the ball bearing is forced out of the cavity when:

$$F_{ball}h > F_{spring}r \cos \phi \quad \text{Equation 6}$$

$$F_{ball}h > KX\, r \cos \phi \quad \text{Equation 7}$$

where K is the spring constant and X is preload distance).

Solving to eliminate the temporary internal variable ($F_{ball}$), the detent ball 624 will be forced out of the detent 614 according to the following relationship:

$$(F_{shaft} 180H/\pi R\omega - \mu_{o\text{-}ring} F_{shaft} - N_{\mu helix} \cos \Theta)h > KXr \cos \phi \quad \text{Equation 8}$$

Figure 26:
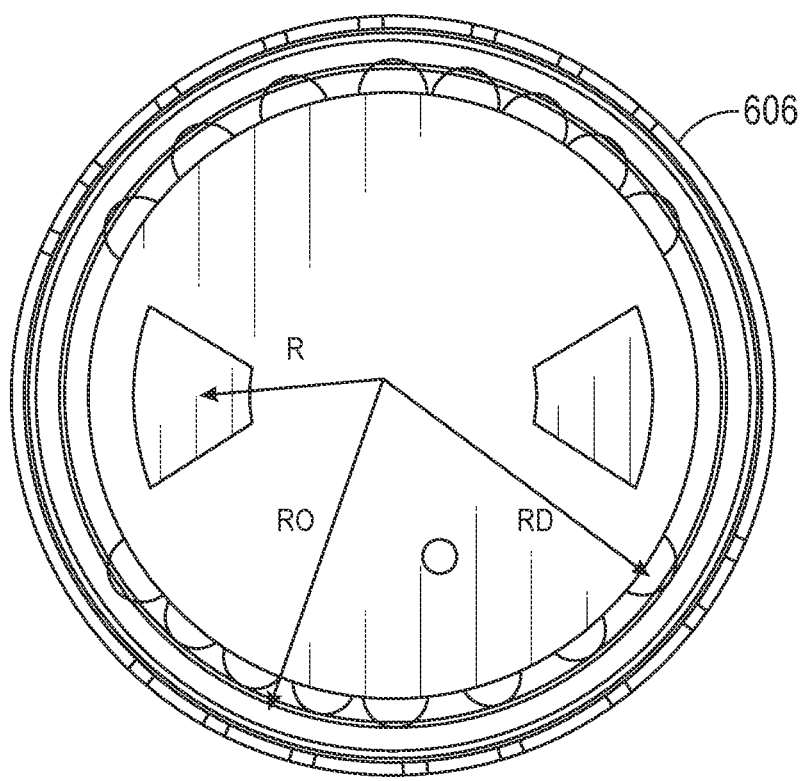
FIG. 26 shows an illustration of radial dimensions of helixes and detents of a handle consistent with at least one example of this disclosure.

The above analysis was a two-dimensional representation. When viewed along the major axis it is clear the four terms actually occur at three different radii. With reference to FIG. 26, the shaft force and frictional engagement between the helixes 608/610 occur at R; the frictional force of the O-ring 612 occurs at $R_{o\text{-}ring}$ and the force of the detent occurs at $R_d$. This aspect of the design allows both the O-ring and detent forces to have a significant mechanical advantage over the force imposed by the drive shaft, which can be applied at approximately one half the radius. This means that in addition to Equation 7 above, the ratio between the force applied by driver on through the helices 608/610 relative to the forces felt by the O-ring 612 and the detents 614/624 are reduced by $R/R_o$ and $R/R_d$, respectively.

The equation $$(F_{shaft} 180H/\pi R\omega - \mu_{o\text{-}ring} F_{shaft} - N_{\mu helix} \cos \Theta)h > KXr \cos \phi \quad \text{Equation 9}$$

demonstrates the designer may use the following variables to hold the force setting securely, despite repeated impact to change the setting.

With respect to the different radii shown in the orthogonal view, the design places the O-ring 612 and detents 614/624 as distant from the center as possible, providing mechanical advantage lowering the chance that impacts from the drive rod will release the detent 614/624 and increasing the relative force provided by the O-ring 612. The designer may use either analysis independently or together in combination to provide the design objectives.

NOTES

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) can be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features can be grouped together to streamline the disclosure. This should not be interpreted as intending that an unclaimed disclosed feature is essential to any claim. Rather, inventive subject matter can lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. A bi-spring surgical impact tool comprising:
    a housing;
    an elongated drive rod disposed in the housing and including an impact flange in a mid-region thereof;
    a tool implement mounted to a first end of the elongated drive rod;
    an impact shuttle mounted on the elongated drive rod and including first and second impact surfaces opposing opposite faces of the impact flange and including a plurality of annular teeth on an exterior surface;
    a first spring disposed against a first end of the impact shuttle;
    a second spring disposed against a second end of the impact shuttle;
    a motor having a drive shaft; and
    a partial tooth pinion attached to the drive shaft and movable for engagement with the plurality of annular teeth of the impact shuttle.

2. The bi-spring surgical impact tool of claim 1, wherein the housing includes a handle and further comprising a battery pack mountable to the handle.

3. The bi-spring surgical impact tool of claim 1, wherein the drive rod is supported by a rear end cap and a forward end cap of the housing.

4. The bi-spring surgical impact tool of claim 1, wherein the impact shuttle is supported on the elongated drive rod by a forward bearing and a rearward bearing.

5. The bi-spring surgical impact tool of claim 1, wherein the first spring and the second spring are formed integrally with the impact shuttle.

6. The bi-spring surgical impact tool of claim 1, wherein a rear end of the elongated drive rod includes a stop collar at a rear end thereof.

7. The bi-spring surgical impact tool of claim 1, further comprising a motor block supporting a pair of bearings that support the drive shaft of the motor and defining an opening for receiving the elongated drive rod and the impact shuttle therein.

8. The bi-spring surgical impact tool of claim 1, further comprising a force control mechanism for adjusting a force level of the bi-spring surgical impact tool by selectively limiting an amount of travel of the elongated drive rod within the housing.

9. The bi-spring surgical impact tool of claim 8, wherein the force control mechanism includes a shaft helix member fixed to a rear end of the elongated drive rod and including a first helix surface that engages a corresponding second helix surface adjustably disposed within a rotary member.

10. The bi-spring surgical impact tool of claim 9, wherein the rotary member includes a plurality of detents, the force control mechanism including a yoke supporting a ball member in engagement with the plurality of detents in order to secure the rotary member in a plurality of positions.

11. The bi-spring surgical impact tool of claim 10, wherein a radius of each detent of the plurality of detents is larger than a radius of the first and second helix surfaces.

12. The bi-spring surgical impact tool of claim 10, wherein a radius of each detent of the plurality of detents is approximately twice a radius of an average helix radius.

13. The bi-spring surgical impact tool of claim 9, wherein the shaft helix member includes a pair of first helix surfaces and the rotary member includes a pair of second helix surfaces that engage the pair of first helix surfaces.

14. A bi-spring surgical impact tool comprising:
   a housing;
   an elongated drive rod disposed in the housing and including an impact flange in a mid-region thereof;
   a tool implement mounted to a first end of the elongated drive rod;
   an impact shuttle mounted on the elongated drive rod and including first and second impact surfaces opposing opposite faces of the impact flange and including a plurality of gear teeth;
   a first spring disposed against a first end of the impact shuttle;
   a second spring disposed against a second end of the impact shuttle;
   a motor including a drive shaft;
   a pinion attached to the drive shaft and movable for engagement with the plurality of gear teeth of the impact shuttle; and
   a force control mechanism for adjusting a force level of the bi-spring surgical impact tool by selectively limiting an amount of travel of the elongated drive rod within the housing.

15. The bi-spring surgical impact tool of claim 14, wherein the drive rod is supported by a rear end cap and a forward end cap of the housing.

16. The bi-spring surgical impact tool of claim 14, wherein the impact shuttle is supported on the elongated drive rod by a forward bearing and a rearward bearing.

17. The bi-spring surgical impact tool of claim 14, wherein the first spring and the second spring are formed integrally with the impact shuttle.

18. The bi-spring surgical impact tool of claim 14, wherein a rear end of the elongated drive rod includes a stop collar at a rear end thereof.

19. The bi-spring surgical impact tool of claim 14, further comprising a motor block supporting a pair of bearings that support the drive shaft of the motor and including an opening for receiving the elongated drive rod and the impact shuttle therein.

20. The bi-spring surgical impact tool of claim 14, wherein the force control mechanism includes a shaft helix member fixed to a rear end of the drive rod and including a first helix surface that engages a corresponding second helix surface adjustably disposed within a rotary member.

* * * * *